(12) United States Patent
Chapple

(10) Patent No.: US 6,610,908 B1
(45) Date of Patent: Aug. 26, 2003

(54) MANIPULATION OF LIGNIN COMPOSITION IN PLANTS USING A TISSUE-SPECIFIC PROMOTER

(75) Inventor: Clinton C. S. Chapple, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/214,139

(22) PCT Filed: Jul. 18, 1997

(86) PCT No.: PCT/US97/12624

§ 371 (c)(1),
(2), (4) Date: Aug. 26, 1999

(87) PCT Pub. No.: WO98/03535

PCT Pub. Date: Jan. 29, 1998

Related U.S. Application Data

(60) Provisional application No. 60/032,908, filed on Dec. 16, 1996, and provisional application No. 60/022,228, filed on Jul. 19, 1996.

(51) Int. Cl.$^7$ .............................. A01H 1/00; C12N 5/04; C12N 15/82
(52) U.S. Cl. ...................... 800/287; 536/23.1; 536/23.6; 536/24.1; 435/320.1; 435/468; 435/410; 435/419; 435/69.1; 800/278; 800/295; 800/320.1; 800/320.2; 800/320.3; 800/317.3; 800/319
(58) Field of Search .............................. 536/23.1, 23.6, 536/24.1; 435/320.1, 468, 410, 419, 69.1; 800/278, 287, 295, 284, 320.1, 320.2, 320.3, 317.3, 319

(56) References Cited

U.S. PATENT DOCUMENTS 5,451,514 A 9/1995 Boudet et al.
5,981,837 A * 11/1999 Chapple .................... 800/278

OTHER PUBLICATIONS

Campbell, Malcolm M.; Sederoff, Ronald R., Variation in Lignin Content and Composition, Plant Physiol. vol. 110, pp. 3–13 (1996).

Douglas, Carl J., Phenylpropanoid metabolism and lignin biosynthesis: from weeds to trees, Trends in Plant Science, Jun. 1996, vol. 1, No. 6, pp. 171–178, ©Elsevier Science Ltd. 1996.

Ni, Weiting: Paiva, Nancy L.; Dixon, Richard A., Reduced lignin in transgenic plants containing a caffeic acid o–methyltransferase antisense gene, Transgenic Research 3, pp. 120–126, ©1994 Chapman & Hall.

Atanassova, Rossitza; Favet, Noelle; Martz, Francoise; Chabbert, Brigitte; Tollier, Marie–Therese; Monties, Bernard; Fritig, Bernard; Legrand, Michel, Altered lignin composition in transgenic tobacco expressing o–methyltransferase sequences in sense and antisense orientation, The Plant Journal, 8 (4), 465–477, 1995.

Halpin, Claire; Knight, Mary E.; Foxon, Geoffrey A.; Campbell, Malcolm M.; Boudet, Alain M.; Boon, Jaap J.; Chabbert, Brigitte; Tollier, Marie–Therese; Schuch, Wolfgang, Manipulation of lignin quality by downregulation of cinnamyl alcohol dehydrogenase, The Plant Journal, 6 (3), pp. 339–350, 1994.

Baucher, Marie; Chabbert, Brigitte; Pilate, Gilles; Van Doorsselaere, Jan; Tollier, Marie–Therese; Petit–Conil, Michel; Cornu, Daniel; Monties, Bernard; Van Montagu, Marc; Inze, Dirk; Jouanin, Lise; Boerjan, Wout, Red Xylem and Higher Lignin Extractability by Down–Regulating a Cinnamyl Alcohol Dehydrogenase in Poplar, Plant Physiol. 112, pp. 1479–1490, 1996.

Lacombe, Eric; Hawkins, Simon; Van Doorsselaere, Jan; Piquemal, Joel; Goffner, Deborah; Poeydomenge, Odile; Boudet, Alain–M; Grima–Pettenati, Jacqueline, Cinnamoyl CoA reductase, the first committed enzyme of the lignin branch biosynthetic pathway: cloning, expression and phylogenetic relationships, The Plant Journal, 11 (3), pp. 429–441, 1997.

Meyer, K., Cusumano, Joanne C., Somerville, Chris, and Chapple, Clint C.S., Ferulate–5–hydroxylase from *Arabidopsis thaliana* defines a new family of cytochrome P450–dependent monoooxygenases, Proc. Natl. Acad. Sci. USA, vol. 93, pp. 6869–6874, Jul. 1996, Biochemistry.

Chapple, Clint C.S., Vogt, Thomas, Ellis, Brian E., and Somerville, Chris R., "An Arabidopsis Mutant Defective in the General Phenylpropanoid Pathway," The Plant Cell, vol. 4, 1413–1424, Nov. 1992, ©1992 American Society of Plant Physiologists.

Chapple, Clint C.S., "An cDNA Encoding a Novel Cytochrome P450–Dependent Monooxygenase from *Arabidopsis thaliana*," Plant Physiol., vol. 108, pp. 875–876 (1995).

(List continued on next page.)

Primary Examiner—David Guzo
(74) Attorney, Agent, or Firm—Woodard, Emhardt, Moriarty, McNett & Henry LLP

(57) ABSTRACT

The present invention relates to methods and materials in the field of molecular biology, the manipulation of the phenylpropanoid pathway and the regulation of proteins synthesis through plant genetic engineering. More particularly, the invention relates to the introduction of a foreign nucleotide sequence into a plant genome, wherein the introduction of the nucleotide sequence effects an increase in the syringyl content of the plant's lignin. In one specific aspect, the invention relates to methods for modifying the plant lignin composition in a plant cell by the introduction there into of a foreign nucleotide sequence comprising at issue specific plant promoter sequence and a sequence encoding an active ferulate-5-hydroxylase (F5H) enzyme. Plant transformants harboring an inventive promoter-F5H construct demonstrate increased levels of syringyl monomer residues in their lignin, rendering the polymer more readily delignified and, thereby, rendering the plant more readily pulped or digested.

18 Claims, 10 Drawing Sheets

(2 of 10 Drawing Sheet(s) Filed in Color)-

OTHER PUBLICATIONS

Grand, Claude, "Ferulic acid 5–hydroxylase: a new cytochrome P–450–dependent enzyme from higher plant microsomes involved in lignin synthesis," FEBS Letters, vol. 169, No. 1, pp. 7–11, Published by Elsevier Science Publishers B.V., Apr. 9, 1984, Federation of European Biochemical Societies.

Van Doorsselaere, Jan, Baucher, Marie, Chognot, Emmanuelle, Chabbert, Brigitte, Tollier, Marie–Therese, Petit–Conil, Michel, Leple, Jean–charles, Pilate, Gilles, Cornu, Daniel, Monties, Bernard, Van Montagu, Marc, Inze, Dirk, Boerjan, Wout and Jouanin, Lise, "A novel lignin in poplar trees with a reduced caffeic acid/5–hydroxyferulic acid o–methyltransferase activity," The Plant Journal, vol. 8, pp. 855–864, 1995.

Dwivedi, Upendra N., Campbell, Wilbur H., Yu, Jun, Datla, Raju S.S., Bugos, Robert C., Chiang, Vincent L., and Podila, Gopi K., "Modification of lignin biosynthesis in transgenic Nicotiana through expression of an antisense o–methyltransferase gene from Populus," Plant Molecular Biology, 26:61–71, 1994, Kluwer Academic Publishers, Printed in Belgium.

Goffner, D., Joffroy, I., Grima–Pettenati, J., Halpin, C., Knight, M.E., Schuch, W., and Boudet, A.M., "Purification and characterization of isoforms of cinnamyl alcohol dehydrogenase from *Eucalyptus xylem*," Planta (Springer–Verlag) (1992) 188:48–53.

Bell–Lelong, Dolly A., Cusumano, Joanne C., Meyer, Knut and Chapple, Clint, "Cinnamate–4–Hydroxylase Expression in Arabidopsis," Plant Physiol. (1997) 113:729–738.

Boudet A. M. et al., *Lignin Genetic Engineering*, Molecular Breeding, NL, Kluwer Academic Publishers, Dordrecht, vol. 2, 1996, pp. 25–39.

Osakabe, Yuriko et al., Structure and Tissue–Specific Expression of Genes for Phenylalanine Ammonia–lyase From a Hybrid Aspen, Populus Kitakamiensis, Plant Science (Limerick), vol. 105, No. 2, 1995, pp. 217–226.

Shiokawa et al., Expression Analysis of a 1–16 Cinnamic Acid 4–Hydroxylase Gene from a Hybrid Aspen, Populus Kitakamiensis, Chemical Abstracts and Indexes, US, American Chemical Society, Columbus, vol. 13, No. 125, Sep. 23, 1996.

WO 97 23599 A (Chapple, Clint; Du Pont (US): Purdue Research Foundation (US) Jul. 3, 1997. (entire document).

WO 98 11205 A (Fletcher Challenge Forests Lim; Genesis Research & Dev. Corp LI (NZ) 19 Mar. 1998. (p. 10, line 18—p. 11, line 9).

* cited by examiner

MANIPULATION OF LIGNIN COMPOSITION IN PLANTS USING A TISSUE-SPECIFIC PROMOTER

REFERENCES TO RELATED APPLICATIONS

This application claims the benefit of U.S. Provisional Application No. 60/022,228, filed Jul. 19, 1996, and U.S. Provisional Application No. 60/032,908, filed Dec. 16, 1996, each of which is hereby incorporated by reference herein in its entirety.

This invention was made with government support under the following grant: number DE-FG02-94ER20138 awarded by the Division of Energy Biosciences, United States Department of Energy. The government has certain rights in the invention.

BACKGROUND OF THE INVENTION

1. Field of the Invention

The present invention relates to methods and materials in the field of molecular biology and the regulation of protein synthesis through plant genetic engineering. More particularly, the invention relates to the introduction of a foreign nucleotide sequence into a plant genome, wherein the introduction of the nucleotide sequence effects an increase in the syringyl content of lignin synthesized by the plant. Specifically, the invention relates in one aspect to methods for modifying the lignin composition in a plant cell by the introduction thereinto of a foreign nucleotide sequence comprising a tissue-specific plant promoter sequence and a coding sequence encoding an active ferulate-5-hydroxylase (F5H) enzyme. Plant transformants harboring an inventive promoter-F5H construct demonstrate increased levels of syringyl monomer residues in lignin synthesized thereby, rendering the polymer more readily delignified and, thereby, rendering the plant more readily pulped or digested.

2. Discussion of Related Art

Lignin is one of the major products of the general phenylpropanoid pathway, set forth in FIG. 1, and is one of the most abundant organic molecules in the biosphere (Crawford, (1981) Lignin Biodegradation and Transformation, New York: John Wiley and Sons). Referring to FIG. 1, lignin biosynthesis via the phenylpropanoid biosynthetic pathway is initiated by the conversion of phenylalanine into cinnamate through the action of phenylalanine ammonia lyase (PAL). The second enzyme of the pathway is cinnamate-4-hydroxylase (C4H), a cytochrome P450-dependent monooxygenase (P450) which is responsible for the conversion of cinnamate to p-coumarate. The second hydroxylation of the pathway is catalyzed by a relatively ill-characterized enzyme, p-coumarate-3-hydroxylase (C3H), whose product is caffeic acid. Caffeic acid is subsequently O-methylated by caffeic acid/5-hydroxyferulic acid O-methyltransferase (OMT) to form ferulic acid, a direct precursor of lignin. The last hydroxylation reaction of the general phenylpropanoid pathway is catalyzed by F5H. The 5-hydroxyferulate produced by F5H is then O-methylated by OMT, the same enzyme that carries out the O-methylation of caffeic acid. This dual specificity of OMT has been confirmed by the cloning of the OMT gene, and expression of the protein in E. coli (Bugos et al., Plant Mol. Biol. 17, 1203, (1991); Gowri et al., (1991) Plant Physiol., 97, 7, (1991)).

Recently, a different route for the biosynthesis of lignin monomers has received attention (Kneusel et al., Arch. Biochem. Biophys. 269, 455, (1989); Kühnl et al., Plant Science 60, 21, (1989); Pakusch et al., Arch. Biochem. Biophys. 271, 488, (1989); Pakusch et al., Plant Physiol. 95, 137, (1991); Schmitt et al., Jour. Biol. Chem. 266, 17416, (1991); Ye et al., Plant Cell 6, 1427, (1994); Ye and Varner, Plant Physiol. 108, 459, (1995)). This so-called "alternative" pathway involves the activation of p-coumaric acid to its coenzyme A thioester, followed by hydroxylation and methylation reactions that generate feruloyl-CoA as the product of the pathway. Considering that ferulic acid can also be synthesized by the free acid pathway and can be activated to its CoA thioester by (hydroxy)cinnamoyl CoA ligate (4CL), lignin monomer biosynthesis probably occurs via a cross-linked network of pathways. Indeed, the continued accumulation of guaiacyl lignin in OMT suppressed plants (Atanassova et al., Plant J. 8, 465, (1995) 1995; Van Doorsselaere et al., Plant J. 8, 855, (1995)) indicates that the alternative pathway may be a major contributor to lignin biosynthesis in woody plants. Both the conventional "free acid" pathway and the "alternative" pathway have been reported to be developmentally regulated, providing different routes for the synthesis of lignin monomers in different cell types (Ye and Varner, supra). This differential gene regulation may be one of the mechanisms by which lignin monomer composition is controlled.

The committed steps of lignin biosynthesis are catalyzed by (hydroxy)cinnamoyl CoA reductase (CCR) and (hydroxy)cinnamoyl alcohol dehydrogenase (CAD), which ultimately generate coniferyl alcohol from ferulic acid and sinapoyl alcohol from sinapic acid. Coniferyl alcohol and sinapoyl alcohol are polymerized by extracellular oxidases to yield guaiacyl lignin and syringyl lignin respectively, although syringyl lignin is more accurately described as a co-polymer of both monomers.

Although ferulic acid, sinapic acid, and in some cases p-coumaric acid are channeled into lignin biosynthesis, in some plants these compounds are precursors for soluble secondary metabolites. For example, in Arabidopsis, sinapic acid serves as a precursor for lignin biosynthesis but it also channeled into the synthesis of soluble sinapic acid esters. In this pathway, sinapic acid is converted to sinapoylglucose which serves as an intermediate in the biosynthesis of sinapoylmalate (FIG. 1). Sinapic acid and its esters are fluorescent and may be used as a marker of plants deficient in those enzymes needed to produce sinapic acid (Chapple et al., Plant Cell 4, 1413, (1992)).

In nature, lignification, or integration of lignin into the plant secondary cell wall, provides rigidity and structural integrity to wood and is in large part responsible for the structural integrity of tracheary elements in a wide variety of plants, giving them the ability to withstand tension generated during transpiration. Lignin also imparts decay resistance to the plant secondary cell wall and is thought to have been essential to the evolution of terrestrial plants. Lignin is well suited to these capacities because of its physical characteristics and its resistance to biochemical degradation. Unfortunately, this same resistance to degradation has a significant impact on the utilization of lignocellulosic plant material (Whetten et al, Forest Ecol. Management 43, 301, (1991)).

In angiosperms, lignin is composed mainly of two aromatic monomers which differ in their methoxyl substitution pattern. As described above, precursors for lignin biosynthesis are synthesized from L-phenylalanine via the phenylpropanoid pathway which provides ferulic acid (4-hydroxy-3-methoxycinnamic acid) and sinapic acid (3,5-dimethoxy-4-hydroxycinnamic acid) for the synthesis of guaiacyl- and syringyl-substituted lignin monomers, respectively. Two cytochrome P450-dependent monoxygenases (450s) are required for the synthesis of lignin monomers. C4H catalyzes the second step of the phenylpropanoid pathway, the hydroxylation of the aromatic ring of cinnamic acid at the para position, and its activity is required for the biosynthesis of all lignin precursors. Ferulate-5-hydroxylase (F5H) catalyzes the meta-hydroxylation of ferulic acid in the monomer-specific pathway branch required for sinapic acid an syringyl lignin biosynthesis.

The balance between guaiacyl and syringyl units in lignin varies between plant species, within a given plant, and even within the wall of a single plant cell. For example, the lignin of the mature Arabidopsis rachis (flowering stem) contains guaiacyl and syringyl residues in an overall ratio of approximately 4:1; however, this ratio is not constant throughout plant development. The syringyl content of the rachis increases from less than 6 mol % within the apical 4 cm of the bolt to over 26 mol % near the base of the inflorescence. Histochemical staining of Arabidopsis rachis cross-sections indicates that syringyl lignin biosynthesis is also developmentally regulated in a tissue-specific manner. Accumulation of syringyl lignin (i.e., lignin synthesized from syringyl and guaiacyl monomers) is restricted to the cells of the sclerified parenchyma that flank the vascular bundles while guaiacyl lignin (i.e. lignin synthesized from guaiacyl monomers only) is deposited only in the cells of the vascular bundle. The increase in syringyl lignin content during rachis development is a consequence of sclerified parenchyma maturation as these cells undergo secondary thickening after the vascular bundle has been formed from the cells of the procambium.

The monomeric composition of lignin has significant effects on its chemical degradation during industrial pulping (Chiang et al., Tappi, 71, 173, (1988). The guaiacyl lignins (derived from ferulic acid) characteristic of softwoods such as pine, require substantially more alkali and longer incubations during pulping in comparison to the guaiacyl-syringyl lignins (derived from ferulic acid and sinapic acid) found in hardwoods such as oak. The reasons for the differences between these two lignin types has been explored by measuring the degradation of model compounds such as guaiacylglycerol-guaiacyl ether, syringylglycerol-guaiacyl ether, and syringylglycerol-(4-methylsyringyl) ether (Kondo et al., Holzforschung, 41, 83, (1987)) under conditions that mimic those used in the pulping process. In these experiments, the mono- and especially di-syringyl compounds were cleaved three to fifteen times faster than their corresponding diguaiacyl homologues. These model studies are in agreement with studies comparing the pulping of Douglas fir and sweetgum wood where the major differences in the rate of pulping occurred above 150 C. where arylglycerol-aryl ether linkages were cleaved (Chiang and Funaoka, Holzforschung, 44, 309, (1990)).

Another factor affecting chemical degradation of the two lignin forms may be the condensation of lignin-derived guaiacyl and syringyl residues to form diphenylmethane units. The presence of syringyl residues in hardwood lignins leads to the formation of syringyl-containing diphenylmethane derivatives that remain soluble during pulping, while the diphenylmethane units produced during softwood pulping are alkali-insoluble and thus remain associated with the cellulosic products (Chiang et al., Holzforschung, 44, 147, (1990); Chiang and Funaoka, supra). Further, it is thought that the abundance of 5–5'-diaryl crosslinks that can occur between guaiacyl residues contributes to resistance to chemical degradation. This linkage is resistant to alkali cleavage and is much less common in lignin that is rich in syringyl residues because of the presence of the 5-O-methyl group in syringyl residues. Thus, the incorporation of syringyl residues results in what is known as "non-condensed lignin", a polymer that is significantly easier to pulp than condensed lignin.

Similarly, lignin composition and content in grasses is a major factor in determining the digestibility of lignocellulosic materials that are fed to livestock (Jung, H. G. & Deetz, D. A. (1993) Cell wall lignification and degradability in Forage Cell Wall Structure and Digestibility (H. G. Jung, D. R. Buxton, R. D. Hatfield, and J. Ralph eds), ASA/CSSA/SSSA Press, Madison, Wis.) The incorporation of the lignin polymer into the plant cell wall prevents microbial enzymes from having access to the cell wall polysaccharides that make up the plant cell wall. As a result, these polysaccharides are substantially unavailable for digestion by livestock, and much of the valuable carbohydrates contained within animal feedstock passes through the animals undigested. Thus, an increase in the dry matter of grasses over the growing season is counteracted by a decrease in digestibility causes principally by increased cell wall lignification. In light of the above background, it is clear that biotechnological modification or manipulation of lignin monomer composition is economically desirable, as it provides the ability to significantly decrease the cost of pulp production and to increase the nutritional value of animal feed stocks thereby also enhancing their economic value.

The mechanism(s) by which plants control lignin monomer composition has been the subject of much speculation. As mentioned above, gymnosperms do not synthesize appreciable amounts of syringyl lignin. In angiosperms, syringyl lignin deposition is developmentally regulated: primary xylem contains guaiacyl lignin, while the lignin of secondary xylem and sclerenchyma is guaiacyl-syringyl lignin (Venverloo, Holzforschung 25, 18 (1971); Chapple et al., supra). No plants have been found to contain purely syringyl lignin. It is still not clear how this specificity is controlled; however, a number of enzymatic steps have previously been proposed as sites for the control of lignin monomer compositions and at least five possible enzymatic control sites exist, namely OMT, F5H, 4CL, CCR, and CAD. For example, the substrate specificities of OMT (Shimada et al., Phytochemistry, 22, 2657, (1972); Shimada et al., Phytochemistry, 12, 2873, (1973); Gowri et al., supra; Bugos et al., supra) and CAD (Sarni et al., Eur. J. Biochem., 139, 259, (1984); Goffner et al., Planta., 188, 48, (1992); O'Malley et al., Plant Physiol., 98, 1364, (1992)) are correlated with the differences in lignin monomer composition seen in gymnosperms and angiosperms, and the expression of 3CL isozymes (Grand et al., Physiol. Veg. 17, 433, (1979); Grand et al., Planta., 158, 255, (1983)) has been suggests to be related to the tissue specificity of lignin monomer composition seen in angiosperms.

Although there are at least five possible enzyme targets, much attention has been directed recently to investigating the use of OMT and CAD to manipulate the lignin monomer composition in transgenic plants (Dwivedi et al., Plant Mol. Biol. 26, 61, (1994); Halpin et al., Plant J. 6, 339, (1994); Ni et al., Transgen, Res. 3, 120 (1994). Atanassova et al., supra: Van Doorsselaere et al., supra). Most of these studies have focused on sense and antisense suppression of OMT expression. This approach has met with variable results, probably owing to the degree of OMT suppression achieved in the various studies. The most dramatic effects were seen by using homologous OMT constructs to suppress OMT expression in tobacco (Atanassova et al., supra) and poplar (Van Doorsselaere et al., supra). Both of these studies found that as a result of transgene expression, there was a decrease in the content of syringyl lignin and a concomitant appearance of 5-hydroxyguaiacyl residues. As a result of these studies, Van Doorsselaere et al., (WO 9305160) disclose a method for the regulation of lignin biosynthesis through the genomic incorporation of an OMT gene in either the sense of anti-sense orientation. In contrast, Dixon et al. (WO 9423044) demonstrate the reduction of lignin content in plants transformed with an OMT gene, rather than a change in lignin monomer composition.

Similar research has focused on the suppression of CAD expression. The conversion of coniferaldehyde and sinapaldehyde to their corresponding alcohols in transgenic tobacco plants has been modified with the incorporation of an A. cordata CAD gene in anti-sense orientation (Hibino et al., Biosci. Biotechnol. Biochem. 59, 929, (1995)). A similar effort aimed at antisense inhibition of CAD expression generated a lignin with increased aldehyde content, but only a modest change in lignin monomer composition (Halpin et al, supra). This research has resulted in the disclosure of methods for the reduction of CAD activity using sense and anti-sense expression of a cloned CAD gene to effect inhibition of endogenous CAD expression in tobacco [Boudet et al., (U.S. Pat. No. 5,451,514) and Walter et al., (WO 9324638); Bridges et al., (CA 2005597)]. None of these strategies, however, increased the syringyl content of lignin, a trait that is correlated with improved digestibility and chemical degradability of lignocellulosic material (Chiang et al., supra. Chiang and Funaoka, supra; Jung et al., supra).

In view of this background, the present invention involves producing transformed plants having increased levels of syringyl residues in their lignins to facilitate chemical degradation of the lignin. Increased syringyl content in lignin produced by a plant transformed in accordance with the invention is achieved by modifying the enzyme pathway responsible for the production of lignin monomers in a manner distinct from those attempted previously. Specifically, this result is achieved in one preferred aspect of the invention by eliciting over-expression of the enzyme F5H in plant cells undergoing lignin synthesis. The term "expression", as used herein, refers to the production of the protein product encoded by a nucleotide coding sequence. "Over-expression" refers to the production of a gene product in transgenic organisms that exceeds levels of production in normal or non-transformed organisms.

Although F5H is a key enzyme in the biosynthesis of syringyl lignin monomers it has not been exploited to date in efforts to engineer lignin quality. In fact, since the time of its discovery over 30 years ago (Higuchi et al., Can. J. Biochem. Physiol., 41, 613, (1963)) there has been only one demonstration of the activity of F5H published (Grand, C., FEBS Lett. 169, 7, (1984)). Grand demonstrated that F5H from poplar was a cytochrome P450-dependent monooxygenase (P450) as analyzed by the classical criteria of dependence of NADPH and light-reversible inhibition by carbon monoxide. Grand further demonstrated that F5H is associated with the endoplasmic reticulum of the cell. The lack of attention given to F5H in recent years may be attributed in general to the difficulties associated with dealing with membrane-bound enzymes, and specifically to the liability of F5H when treated with the detergents necessary for solubilization (Grand, supra). The most recent discovery surrounding F5H has been made by Chapple et al., (supra) who reported a mutant of Arabidopsis thaliana L. Heynh named fah1 that is deficient in the accumulation of sinapic acid-derived metabolites, including the guaiacyl-syringyl lignin typical of angiosperms. This locus, termed FAH1, encodes F5H.

In spite of sparse information about F5H in the published literature, the present inventor has been successful in the isolation, cloning, and sequencing of the F5H gene (Meyer et al., Proc. Natl. Acad. Sci. USA 93, 6869(1996)). The present inventor has also demonstrated that the stable integration of the F5H gene into the plant genome, where the expression of the F5H gene is under the control of a promoter other than the gene's endogenous promoter (such as, for example, the 35S promoter), leads to an altered regulation of lignin biosynthesis. It has been determined that causing over-expression of the enzyme F5H in Arabidopsis using the 35S promoter allows the plant to produce lignin containing up to 30% of the syringyl monomer. This over-expression may be accomplished by constructing a 35S promoter/F5H construct and transforming a plant host with the construct. Similarly, over-expression of the enzyme F5H in tobacco using the 35S promoter allows the plant to produce lignin in its petioles (leaf stems) containing up to 40% of the syringyl monomer. One problem with this system, however, is that Arabidopsis plants transformed with the construct are unable to produce lignin having syringyl content greater than about 30mol %. Similarly, in tobacco plants transformed with the 35S promoter/F5H construct, no change was observed in the syringyl monomer content of stem lignin which is naturally approximately 50%.

These limitations are overcome by the present invention, which provides in one preferred aspect a genetic construct assembled from a tissue-specific promoter sequence endogenous to plant cells and a nucleotide sequence which encodes the enzyme F5H. The construct may be used to transform plants, thereby providing transformed plants capable of producing lignin having a syringyl content greater than a native plant. For example, an Arabidopsis plant may be transformed in accordance with the invention such that the transformed Arabidopsis plant is capable of producing lignin having syringyl content of greater than about 30 mol %. Furthermore, inventive constructs may be used to transform a tobacco plant such that the transformed tobacco plant is capable of producing lignin in its petioles having a syringyl content of greater than about 40 mol % and such that the transformed tobacco plant is capable of producing stem lignin having a syringyl content of greater than about 50 mol %.

SUMMARY OF THE INVENTION

The present invention relates to the isolation, purification and use of DNA constructs comprising a tissue-specific plant promoter, for example, a C4H promoter, and a nucleotide sequence useful for the modification of lignin biosynthesis such as, for example, an F5H coding sequence. Inventive DNA constructs employing lignification-specific promoters such as the C4H promoter are useful for modifying the quality or quantity of a plants lignin, and specific examples of constructs are provided herein for increasing the syringyl content of a plant's lignin by targeting over-expression of the F5H enzyme to plant cells producing lignin or providing the precursors for lignin biosynthesis. Lignification-specific promoters set for in FIG. 1, such as the C4H promoter are effective in directing gene expression to lignifying cells, and are thus useful promoters for modifying gene expression in these cells via antisense or co-suppression technologies. As discussed in the Background above and set forth in FIG. 1, the F5H enzyme catalyzes an irreversible hydroxylation step that diverts ferulic acid away from the guaiacyl lignin biosynthesis and toward sinapic acid and syringyl lignin biosynthesis. Specifically, F5H catalyzes the reaction of ferulate to 5-hydroxyferulate and over-expression thereof in the proper plant tissues under the control of lignification-specific promoters such as the C4H promoter results in synthesis of lignin having a high syringyl content, i.e., greater than that achieved in prior art plants of the same species.

High syringyl lignins are more readily degraded during the pulping process and during ruminant digestion of lignocellulosic feedstocks. The unaltered morphology of tracheary elements and sclerified parenchyma in transgenic plants depositing lignin highly enriched in syringyl units suggests that this lignin still provides lignified cells with sufficient rigidity to function normally in water conduction and mechanical support. Thus, a surprisingly advantageous result is achieved in accordance with the invention upon increasing the syringyl content of crop species and trees, thereby generating lignins that are easier to digest or extract without detrimental consequences on agricultural performance.

It is presently shown that inventive DNA constructs may advantageously be used according to the invention to transform a plant, thereby providing an inventive transformed plant which produces lignin having a syringyl:guaiacyl ratio that is greater than that of a non-transformed plant of the same species or a plant of the same species transformed using constructs known in the prior art. The present invention thus provides methods for genetically engineering plants to provide inventive transformed plants which may be readily delignified. The invention features DNA constructs comprising a tissue-specific plant promoter sequence and a coding sequence as set forth herein, as well as DNA constructs comprising nucleotide sequences having substantial identity thereto and having similar levels of functionality. Inventive constructs may be inserted into an expression vector to produce a recombinant DNA expression system which is also an aspect of the invention.

In a preferred aspect of the invention, there is provided an isolated nucleic-acid construct comprising a nucleotide sequences which correspond to a regulatory sequence of the C4H genomic sequence set forth in SEQ ID NO:1 and a nucleotide sequence having substantial similarity to the sequence set forth in either SEQ ID NO:2 (F5H genomic nucleotide sequence) or SEQ ID NO:3 (F5H cDNA). In a preferred aspect of the invention, the enzyme encoded thereby preferably has an amino acid sequence having substantial identity to the F5H enzyme set forth in SEQ ID NO:4, wherein the amino acid sequence may include amino acid substitutions, additions and deletions that do not alter the function of the F5H enzyme.

It is an object of the present invention to provide an isolated DNA construct which comprises a tissue-specific promoter and a nucleotide sequence encoding an F5H enzyme, the construct finding advantageous use when incorporated into a vector or plasmid as a transformant for a plant.

Additionally, it is an object of the invention to provide transformed plants which produce lignin having a syringyl content grater than a native plant of the same species, thereby providing resources for the pulping industry which are much more readily and economically delignified, and providing agricultural feedstocks which are much more readily and efficiently digested by livestock.

Further objects, advantages and features of the present invention will be apparent from the detailed description herein.

BRIEF DESCRIPTION OF THE FIGURES

The file of this patent contains at least one drawing executed in color. Copies of this patent with color drawings will be provided by the Patent and Trademark Office upon request and payment of the necessary fee.

Although the characteristic features of this invention will be particularly pointed out in the claims, the invention itself, and the manner in which it may be made and used, may be better understood by referring to the following description taken in connection with the accompanying figures forming a part hereof.

DETAILED DESCRIPTION OF THE INVENTION

Figure 1:
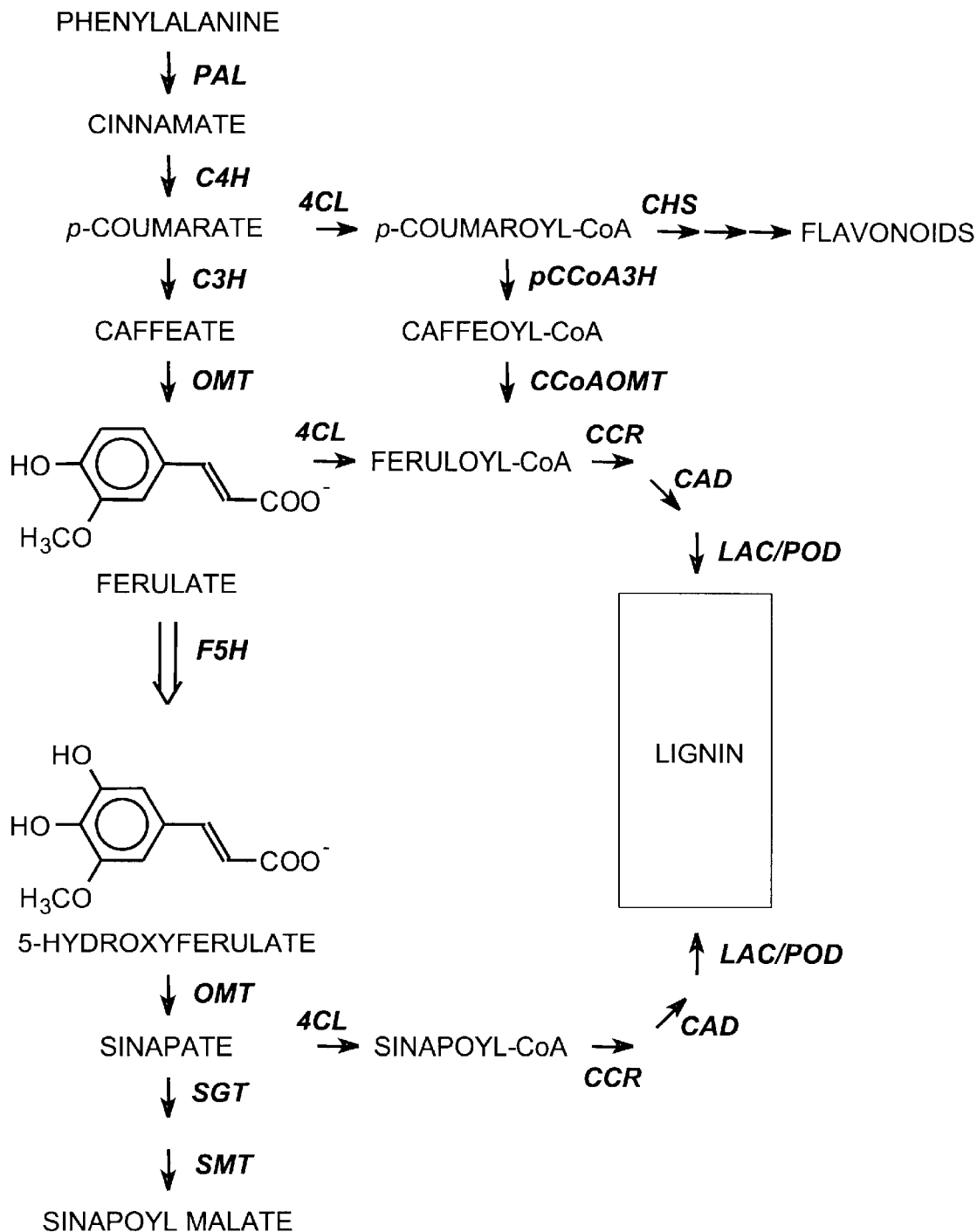
FIG. 1 illustrates the general phenylpropanoid pathway, and associated pathways leading to lignin, sinapate esters, and flavonoids in Arabidopsis. The structures of ferulate and 5-hydroxyferulate are shown to emphasize the reaction catalyzed by ferulate-5-hydroxylase (F5H). The names of enzymes are shown in italics and include phenylalanine ammonia-lyase (PAL), cinnamate-4-hydroxylase (C4H), p-coumarate-3-hydroxylase (C3H), caffeic acid/5-hydroxyferulic acid)-methyltransferase (OMT), sinapic acid:UDPG sinapoyltransferase (SGT), sinapoyl glucose-:malate sinapoyltransferase (SMT), hydroxycinnamoyl-CoA ligase (4CL), p-coumaroyl-CoA-3-hydroxylase (pCCoA3H), caffeoyl-CoAO-methyltransferase (CCoAOMT), hydroxycinnamoyl-CoA reductase (CCR), hydroxycinnamoyl alcohol dehydrogenase (CAD), laccase/peroxidase (LAC/POD) and chalcone synthase (CHS).

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention are described herein being contemplated as would normally occur to one skilled in the art to which the invention pertains.

The present invention relates to DNA constructs that may be integrated into a plant to provide an inventive transformed plant which over-express F5H or another key lignin biosynthesis enzyme, in lignin-producing cells. Over-expression of F5H results in an increased conversion of ferulic acid to sinapic acid, and results in an increase in the syringyl content of the lignin polymer produced by the plant. The present inventor has discovered a novel DNA construct comprising a tissue-specific promoter and a nucleotide coding sequence which encodes an F5H enzyme. When heightened expression of F5H is achieved in a transformed plant in accordance with the present invention, the transformed plant accumulates lignin that is highly enriched in syringyl residues, and thereby is more readily degraded during the pulping process and during ruminant digestion of lignocellulosic feedstocks. As such, advantageous features of the present invention include the transformation of a wide variety of plants of various agriculturally and/or commercially valuable plant species to provide transformed plants having advantageous delignification properties. It is also expected that inventive tissue-specific promoters may be used in conjunction with expression, antisense or cosuppression systems corresponding to other enzymes of the phenylpropanoid pathway, such as, for example, CAD or OMT, to enhance the effect of these systems in lignin-producing cells. While these systems have proven to have certain effects when present in a construct under the control of, for example, the 35S promoter, it is expected that placing the nucleotide sequence under control of a promoter selected in accordance with the present invention will enhance the desired result achieved using expression systems known in the prior art.

Promoters selected for use in accordance with one aspect of the present invention effectively target F5H expression to those tissues that undergo lignification. Preferably, the promoter is one isolated from a gene which encodes an enzyme in the phenylpropanoid pathway. For example, overexpression of F5H may preferably be obtained in target plant tissues using one of the following promoters: phenylalanine ammonia-lyase (PAL), C4H, O-methyltransferase (OMT), (hydroxy)cinnamoyl-CoA ligase (4CL), (hydroxy) cinnamoyl-CoA reductase (CCR), (hydroxy)cinnamoyl alcohol dehydrogenase (CAD), Laccase and caffeic acid/5-hydroxyferulic acid. Most preferably, the promoter used is the C4H promoter. It is not intended, however, that this list be limiting, but only provide examples of promoters which may be advantageously used in accordance with the present invention to provide over-expression of F5H in cells producing lignin or providing precursors for lignin biosynthesis. Although promoter sequences for specific enzymes commonly differ between species, it is understood that the present invention includes promoters which regulates phenylpropanoid genes in a wide variety of plant species. For example, while the C4H promoter of the species Arabidopsis thaliana is set forth in SEQ ID NO:1 herein, it is not intended that the present invention be limited to this sequences, but include sequences having substantial similarity thereto and sequences from different plant species which promote the expression of analogous enzymes of that species' phenylpropanoid pathway.

Similarly, an expression sequence selected for use in accordance with the present invention is one that effectively modifies lignin biosynthesis in tissues that undergo lignification. Preferably, the expression sequences encodes an enzyme in the phenylpropanoid pathway. For example, over-expression, antisense, or cosuppression of lignin biosynthetic genes may preferably be obtained in the target plant tissues using an expression sequence encoding one of the following enzymes: PAL, C4H, OMT, F5H, 4CL, CCR, CAD, and laccase. Most preferably, the sequence used encodes F5H. It is not intended, however, that this list be limiting, but only provide examples of sequences which may be advantageously used in accordance with the present invention to provide over-expression, antisense or cosuppression of lignin biosynthetic enzymes in cells producing lignin or providing precursors for lignin biosynthesis. As sequences encoding related enzymes commonly differ between species, it is understood that the present invention includes genes which encode lignin biosynthetic proteins in a wide variety of plant species. While nucleotide sequences encoding the F5H of the species Arabidopsis thaliana are set forth in SEQ ID NO:2 and SEQ ID NO:3 herein, it is not intended that the present invention be limited to these sequences, but include sequences having substantial similarity thereto and sequences from different plant species that encode enzymes involved in lignin biosynthesis of that species' phenylpropanoid pathway.

While the present invention is intended to encompass constructs comprising a wide variety of promoters and a wide variety of expressible nucleotide sequences, for purposes of describing the invention, one particularly preferred construct will be described as a representative example. It should be understood that this discussion applies equally to constructs prepared or selected in accordance with the invention which comprise a different promoter and/or a different coding sequence. The example described below comprises a C4H promoter and an F5H expression sequence. In this regard, nucleotide sequences advantageously selected for inclusion in a DNA construct according to a preferred aspect of the invention are a C4H regulatory sequence (as set forth in the C4H genomic sequence of SEQ ID NO:1) and either an F5H genomic sequence (as set forth in SEQ ID NO:2) or an F5H cDNA sequence (as set forth in SEQ ID NO:3).

The term "nucleotide sequence" is intended to refer to a natural or synthetic linear and sequential array of nucleotides and/or nucleosides, and derivatives thereof. The terms "encoding" and "coding" refer to the process by which a gene, through the mechanisms of transcription and translation, provides the information to a cell from which a series of amino acids can be assembled into a specific amino acid sequence to produce a functional protein, such as, for example, an active enzyme. It is understood that the process of encoding a specific amino acid sequence may involve DNA sequences having one or more base changes (i.e., insertions, deletions, substitutions) that do not cause a change in the encoded amino acid, or which involve base changes which may alter one or more amino acids, but do not affect the functional properties of the protein encoded by the DNA sequence.

A preferred DNA construct selected or prepared in accordance with the invention expresses an F5H enzyme, or an enzyme having substantial similarity thereto and having a level of enzymatic activity suitable to achieve the advantageous result of the invention. A preferred amino acid sequence encode by the inventive DNA construct is the F5H amino acid sequence set forth in SEQ ID NO:4. The terms "protein, "amino acid sequence" and "enzyme" are used interchangeably herein to designate a plurality of amino acids linked in a serial array. Skilled artisans will recognize that through the process of mutation and/or evolution, proteins of different lengths and having differing constituents, e.g., with amino acid insertions, substitutions, deletions, and the like, may arise that are related to the proteins of the present invention by virtue of (a) amino acid sequence homology; and (b) good functionality with respect to enzymatic activity. For example, an F5H enzyme isolated from one species and/or the nucleotide sequence encoding it, may differ to a certain degree from the sequences set forth herein, and yet have excellent functionality in accordance with the invention. Such an enzyme and/or nucleotide sequence falls directly within the scope of the present invention. While may deletions, insertions, and, especially, substitutions, are not expected to produce radical changes in the characteristics of the protein, when it is difficult to predict the exact effect of the substitution, deletion, or insertion in advance of doing so, one skilled in the art will appreciate that the effect may be evaluated by routine screening assays.

In addition to the F5H protein in this embodiment, therefore, the present invention also contemplates proteins having substantial identity thereto. The term "substantial identity," as used herein with respect to an amino acid sequence, is intended to mean sufficiently similar to have suitable functionality when expressed in a plant transformed in accordance with the invention to achieve the advantageous result of the invention. In one preferred aspect of the present invention, variants having such potential modifications as those mentioned above, which have at least about 50% identity to the amino acid sequence as set forth in SEQ ID NO:4, are considered to have "substantial identity" thereto. Sequences having lesser degrees of identity but comparable biological activity are considered to be equivalents. It is believed that the identity required to maintain property functionality is related to maintenance of the tertiary structure of the protein such that specific interactive sequences will be properly located and will have the desired activity. As such, it is believed that there are discrete domains and motifs within the amino acid sequence which must be present for the protein to retain its advantageous functionality and specificity. While it is not intended that the present invention be limited by any theory by which it achieves its advantageous result, it is contemplated that a protein including these discrete domains and motifs in proper spatial context will retain good enzymatic activity.

It is therefore understood that the invention also encompasses more than the specific exemplary nucleotide sequences. Modifications to the sequence, such as deletions, insertions, or substitutions in the sequence which produce "silent" changes that do not substantially affect the functional properties of the resulting protein molecule are also contemplated. For example, alterations in the nucleotide sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. As a related matter, it is understood that similar base changes may be present in a promoter sequence without substantially affecting is valuable functionality. Such variations to a promoter sequence are also within the purview of the invention.

In a preferred aspect, therefore, the present invention contemplates nucleotide sequences having substantial identity to those set forth in SEQ ID NOS. 1, 2 and 3. The term "substantial identity" is used herein with respect to a nucleotide sequence to designate that the nucleotide sequence has a sequence sufficiently similar to one of those explicitly set forth herein that it will hybridize therewith under moderately stringent conditions, this method of determining identity being well known in the art to which the invention pertains. Briefly, moderately stringent conditions are defined in Sambrook et al., Molecular Cloning: a Laboratory Manual, 2ed. Vol. 1 pp. 101–104, Cold Spring Harbor Laboratory Press (1989) as including the use of a prewashing solution of 5×SSC, 0.5% SDS, 1.0 mM EDTA (pH 8.0) and hybridization and washing conditions of about 55 C, 5×SSC. A further requirement of the term "substantial identity" as it relates to an inventive nucleotide coding sequence in accordance with this embodiment is that it must encode a protein having substantially similar functionality to the F5H enzyme set forth in SEQ ID NO:4, i.e., one which is capable of effecting an increased syringyl content in a plant's lignin composition when over-expressed in the plant's tissues producing lignin or providing the precursors for lignin biosynthesis.

Suitable DNA sequences selected for use according to the invention may be obtained, for example, by cloning techniques using cDNA libraries corresponding to a wide variety of plant species, these techniques being well known in the relevant art, or may be made by chemical synthesis techniques which are also well known in the art. Suitable nucleotide sequences may be isolated from DNA libraries obtained from a wide variety of species by means of nucleic acid hybridization or PCR, using as hybridization probes or primers nucleotide sequences selected in accordance with the invention, such as those set forth in SEQ ID NOS: 1, 2 and 3; nucleotide sequences having substantial identity thereto; or portions thereof. In certain preferred aspects of the invention, nucleotide sequences from a wide variety of plant species may be isolated and/or amplified which encode F5H, or a protein having substantial identity thereto and having suitable activity with respect to increasing syringyl content of the plant's lignin. Nucleotide sequences may also be isolated and/or amplified from a wide variety of plant species which correspond to the C4H promoter, a nucleotide sequence having substantial functional or sequence similarity thereto or a nucleotide sequence having an analogous function in a wide variety of plant species. Nucleotide sequences specifically set forth herein or selected in accordance with the invention may be advantageously used in a wide variety of plant species, including but not limited to the species from which it is isolated.

Inventive DNA sequences can be incorporated into the genomes of plant cells using conventional recombinant DNA technology, thereby making transformed plants capable of producing lignin having increased syringyl content. In this regard, the term "genome" as used herein is intended to refer to DNA which is present in the plant and which is heritable by progeny during propagation of the plant. As such, inventive transgenic plants may alternatively be produced by breeding a transgenic plant made according to the invention with a second plant or selfing an inventive transgenic plant to form an F1 or higher generation plant. Transformed plants and progeny thereof are all contemplated by the invention and are all intended to fall within the meaning of the term "transgenic plant."

Generally, transformation of a plant involves inserting a DNA sequence into an expression vector in proper orientation and correct reading frame. The vector contains the necessary elements for the transcription of the inserted protein-encoding sequences. A large number of vector systems known in the art can be advantageously used in accordance with the invention, such as plasmids, bacteriophage viruses or other modified viruses. Suitable vectors include, but are not limited to the following viral vectors: lambda vector system gt11, gt10. Charon 4, and plasmid vectors such as pB1121, pBR322, pACYC177, pACYC184, pAR series pKK223-3 pUC8, pUC9, pUC18, pUC19, pLG339, pRK290, pKC37, pKC101, pCDNAII, and other similar systems. The DNA sequences are cloned into the vector using standard cloning procedures in the art, for example, as described by Maniatis et al., Molecular Cloning: A Laboratory Manual, Cold Springs Laboratory. Cold Springs Harbor, N.Y. (1982), which is hereby incorporated by reference. The plasmid pB1121 is available from Clontech Laboratories, Palo Alto, Calif. It is understood that related techniques may be advantageously used according to the invention to transform microorganisms such as, for example, Agrobacterium sp., yeast, *E. coli* and Pseudomonas sp.

In order to obtain satisfactory expression of a lignification-related gene such as the F5H nucleotide coding sequence in the proper plant tissues, a tissue-specific plant promoter selected in accordance with the invention must be present in the expression vector. An expression vector according to the invention may be either naturally or artificially produced from parts derived from heterologous sources, which parts may be naturally occurring or chemically synthesized, and wherein the parts have been joined by ligation or other means known in the art. The introduced coding sequence is under control of the promoter and thus will be generally downstream from the promoter. Stated alternatively, the promoter sequence will be generally upstream (i.e., at the 5' end) of the coding sequence. The phrase "under control of" contemplates the presence of such other elements as may be necessary to achieve transcription of the introduced sequence. As such, in one representative example, enhanced F5H production may be achieved by inserting a F5H nucleotide sequence in a vector downstream from and operably linked to a promoter sequence capable of driving tissue-specific high-level expression in a host cell. Two DNA sequences (such as a promoter region sequence and a F5H-encoding sequence) are said to be operably linked if the nature of the linkage between the two DNA sequences does not (1) result in the introduction of a frame-shift mutation, (2) interfere with the ability of the promoter region sequence to direct the transcription of the desired F5H-encoding gene sequence, or (3) interfere with the ability of the desired F5H sequence to be transcribed by the promoter region sequence.

RNA polymerase normally binds to the promoter and initiates transcription of a DNA sequence or a group of linked DNA sequences and regulatory elements (operon). A transgene, such as a nucleotide sequence selected in accordance with the present invention, is expressed in a transformed plant to produce in the cell a protein encoded thereby. Briefly, transcription of the DNA sequence is initiated by the binding of RNA polymerase to the DNA sequence's promoter region. During transcription, movement of the RNA polymerase along the DNA sequence forms messenger RNA ("mRNA") and, as a result, the DNA sequence is transcribed into a corresponding mRNA. This mRNA then moves to the ribosomes of the cytoplasm or rough endoplasmic reticulum which, with transfer RNA ("tRNA"), translates the mRNA into the protein encoded thereby. Proteins of the present invention thus produced in a transformed host then perform an important function in the plant's synthesis of lignin.

It is well known that there may or may not be other regulatory elements (e.g., enhancer sequences) which cooperate with the promoter and a transcriptional start site to achieve transcription of the introduced (i.e., foreign) coding sequence. Also, the recombinant DNA will preferably include a transcriptional termination sequence downstream from the introduced sequence.

Once the DNA construct of the present invention has been cloned into an expression system, it is ready to be transformed into a host plant cell. Plant tissue suitable for transformation in accordance with certain preferred aspects of the invention include whole plants, leaf tissues, flower buds, root tissues, meristems, protoplasts, hypocotyls and cotyledons. It is understood, however that this list is not intended to be limiting, but only provide examples of tissues which may be advantageously transformed in accordance with the present invention. One technique of transforming plants with a DNA construct in accordance with the present invention is by contacting the tissue of such plants with an inoculum of a bacteria transformed with a vector comprising a DNA sequence selected in accordance with the present invention. Generally, this procedure involves inoculating the plant tissue with a suspension of bacteria and incubating the tissue for about 48 to about 72 hours on regeneration medium without antibiotics at about 25–28 C.

Bacteria from the genus Agrobacterium may be advantageously utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants. Another technique which may advantageously be used is vacuum-infiltration of flower buds using Agrobacterium-based vectors.

Another approach to transforming plant cells with a DNA sequence selected in accordance with the present invention involves propelling inert or biologically active particles at plant tissues or cells. This technique is disclosed in U.S. Pat. Nos. 4,945,050, 5,036,006 and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector. Alternatively, the target cell can be surrounded by the vector so that the vector is carried into the cell by the wake of the particle. Biologically active particles (e.g., dried yeast cells, dried bacterium or a bacteriophage, each containing DNA material sought to be introduced) can also be propelled into plant cells. It is not intended, however, that the present invention be limited by the choice of vector or host cell. It should of course be understood that not all vectors and expression control sequences will function equally well to express the DNA sequences of this invention. Neither will all hosts function equally well with the same expression system. However, one of skill in the art may make a selection among vectors, expression control sequences, and hosts without undue experimentation and without departing from the scope of this invention.

Once the recombinant DNA is introduced into the plant tissue, successful transformants can be screened using standard techniques such as the use of marker genes, e.g., genes encoding resistance to antibiotics. Additionally, the level of expression of the foreign DNA may be measured at the transcriptional level, as protein synthesized or by assaying to determine lignin syringyl content.

An isolated DNA construct selected in accordance with the present invention may be utilized in an expression system to increase the syringyl content of lignin in a wide variety of plants, including gymnosperms, monocots and dicots. Inventive DNA constructs are particularly useful in the following plants: alfalfa (Medicago sp.), rice (Oryza sp.), maize (*Zea mays*), oil seed rape (Brassica sp.), forage grasses, and also tree crops such as eucalyptus (Eucalyptus sp.), pine (Pinus ep.), spruce (Picea sp.) and poplar (Populus sp.), as well as Arabidopsis sp. and tobacco (Nicotiana sp).

Those skilled in the art will recognize the commercial and agricultural advantages inherent in plants transformed to have increased or selectively increased expression of F5H and/or of nucleotide sequences which encode proteins having substantial identity thereto. Such plants are expected to have substantially improved delignification properties and, therefore, are expected to be more readily pulped and/or digested compared to a corresponding non-transformed plant.

The invention will be further described with reference to the following specific Examples. It will be understood that these Examples are illustrative and not restrictive in nature.

EXAMPLES

General Methods

Restriction enzyme digestions, phosphorylations, ligations and transformations were done as described in Sambrook et al., Molecular Cloning: A Laboratory Manual, Second Edition (1989) Cold Spring Harbor Laboratory Press. All reagents and materials used for the growth and maintenance of bacterial cells were obtained from Aldrich Chemicals (Milwaukee, Wisc.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "L" means microliter(s), "mL" means milliliter(s). "L" means liter(s), "g" means gram(s), "mg" means milligram(s), "g" means microgram(s), "nm" means nanometer(s), "m" means meter(s), "E" means Einstein(s).

Plant Material

*Arabidopsis thaliana* was grown under a 16 h light/8 h dark photoperiod at 100 E $m^{-2}s^{-1}$ at 24° C. cultivated in Metromix 2000 potting mixture (Scotts, Marysville Ohio). Mutant lines fah1-1 through fah1-5 were identified by TLC as described below. Using their red fluorescence under UV light as a marker, mutant lines fah1-6 fah1-7, and fah1-8 were selected from ethylmethane sulfonate (fah1-6, fah1-7) or fast neutron (fah1-8) mutagenized populations of Landsberg erecta M2 seed. The T-DNA tagged line 3590 (fah1-9) was similarly identified in the DuPont T-DNA tagged population (Feldmann, K. A., Malmberg, R. L., & Dean, C., (1994) *Mutageneses in Arabidopsis* in Arabidopsis, (E. M. Meyerowitz and C. R. Somerville, eds.) Cold Spring Harbor Press). All lines were backcrossed to wild type at least twice prior to experimental use to remove unlinked background mutations. Tobacco plants were grown in a greenhouse under a 16 h light/8 h dark photoperiod at 500 E $m^{-2}s^{-1}$ at 24° C. cultivated in Metromix 2000 potting mixture (Scotts, Marysville Ohio).

Secondary Metabolite Analysis

Leaf extracts were prepared from 100 mg samples of fresh leaf tissue suspended in 1 mL of 50% methanol. Samples were vortexed briefly, then frozen at −70° C. Samples were thawed, vortexed, and centrifuged at 12,000×g for 5 min. Sinapoylmalate content was qualitatively determined following silica gel TLC, in a mobile phase of n-butanol/ethanol/water (4:1:1). Sinapic acid and its esters were visualized under long wave UV light (365 nm) by their characteristic fluorescence.

Southern Analysis

For Southern analysis. DNA was extracted from leaf material (Rogers, et al., (1985) *Plant. Mol. Biol.* 5, 69), digested with restriction endonucleases and transferred to Hybond N+ membrane (Amersham, Cleveland Ohio) by standard protocols. cDNA probes were radiolabelled with $^{32}P$ and hybridized to the target membrane in Denhardt's hybridization buffer (900 mM sodium chloride, 6 mM disodium EDTA, 60 mM sodium phosphate pH 7.4, 0.5% SDS, 0.01% denatured herring sperm DNA and 0.1% each polyvinylpyrrolidone, bovine serum albumin, and Ficoll 400) containing 50% formamide at 42° C. To remove unbound probe, membranes were washed twice at room temperature and twice at 65° C. in 2×SSPE (300 mM sodium chloride, 2 mM disodium EDTA, 20 mM sodium phosphate, pH 7.4) containing 0.1% SDS, and exposed to film.

Northern Analysis

RNA was first extracted from leaf material according to the following protocol. For extraction of RNA, Covey's extraction buffer was prepared by dissolving 1% (w/v) TIPS (triisopropyl-naphthalene sulfonate, sodium salt), 6% (w/v) PAS (p-aminosalicylate, sodium salt) in 50 mM Tris pH 8.4 containing 5% v/v Kirby's phenol. Kirby's phenol was prepared by neutralizing liquified phenol containing 0.1% (w/v) 8-hydroxyquinoline with 0.1 M Tris-HCl pH 8.8. For each RNA preparation, a 1 g samples of plant tissue was ground in liquid nitrogen and extracted in 5 mL Covey's extraction buffer containing 10 L-mercaptoethanol. The sample was extracted with 5 mL of a 1:1 mixture of Kirby's phenol and chloroform, vortexed, and centrifuged for 20 min at 7,000×g. The supernatant was removed and the nucleic acids were precipitated with 500 L of 3 M sodium acetate and 5 mL isopropanol and collected by centrifugation at 10,000×g for 10 min. The pellet was redissolved in 500 L water, and the RNA was precipitated on ice with 250 L 8 M LiCl, and collected by centrifugation at 10,000×g for 10 min. The pellet was resuspended in 200 L water and extracted with an equal volume of chloroform:isoamyl alcohol 94:1 with vortexing. After centrifugation for 2 min at 10,000×g, the upper aqueous phase was removed, and the nucleic acids were precipitated at −20° C. by the addition of 20 L 3 M sodium acetate and 200 L isopropanol. The pellet was washed with 1 mL cold 70% ethanol, dried, and resuspended in 100 L water. RNA content was assayed spectrophotometrically at 260 nm. Samples containing 1 to 10 g of RNA were subjected to denaturing gel electrophoresis as described elsewhere (Sambrook et al., supra).

Extracted RNA was transferred to Hybond N membrane (Amersham, Cleveland Ohio), and probed with radiolabelled probes prepared from cDNA clones. Blots were hybridized overnight, washed twice at room temperature and once at 65° C. in 3×SSC (450 mM sodium chloride, 45 mM sodium citrate, pH 7.0) containing 0.1% SDS, and exposed to film.

Identification of cDNA and Genomic Clones cDNA and genomic clones for F5H were identified by standard techniques using a 2.3 kb SacII/EcoRI fragment from the rescued plasmid (pCC1) (Example 2) as a probe. The cDNA clone pCC30 was identified in the PRL2 library (Newman et al., Plant Physiol. 106, 1241, (1994)) kindly provided by Dr. Thomas Newman (DOE Plant Research Laboratory, Michigan State University, East Lansing, Mich.). A genomic cosmid library of *Arabidopsis thaliana* (ecotype Landsberg erecta) generated in the binary cosmid vector pBIC 20 (Example 3) (Meyer et al., *Science* 264, 1452, (1994) was screened with the radiolabelled cDNA insert derived from pCC30. Genomic inserts in the pBIC20 T-DNA are flanked by the neomycin phosphotransferase gene for kanamycin selection adjacent to the T-DNA right border sequence, and the -glucuronidase gene for histochemical selection adjacent to the left border. Positive clones were characterized by restriction digestion and Southern analysis in comparison to Arabidopsis genomic DNA.

Plant transformation

Transformation of *Arabidopsis thaliana* was performed by vacuum infiltration (Bent et al., Science 265, 1856, (1994) with minor modifications. Briefly, 500 mL cultures of transformed Agrobacterium harboring the pBIC20-F5H cosmid, the pGA482-35S-F5H construct, or the pGA482 C4H-F5H construct were grown to stationary phase in Luria broth containing 10 mg L$^{-1}$ rifampicin and 50 mg L$^{-1}$ kanamycin. Cells were harvested by centrifugation and resuspended in 1 L infiltration media containing 2.9 g MS salts (Murashige and Skoog, *Physiol. Plant.* 15, 473, (1962)), Gamborg's B5 vitamins (Gamborg et al., *Exp. Cell Res.* 50, 151, (1968)), 0.5 g MES, 50 g sucrose. 44 nM benzylaminopurine, and 200 L Silwet L-77 (OSI Specialties) at pH 5.7. Bolting Arabidopsis plants (T$_0$ generation) that were 5 to 10 cm tall were inverted into the bacterial suspension and exposed to a vacuum (>500 mm of Hg) for three to five min. Infiltrated plants were returned to standard growth conditions for seed production. Transformed seedlings (T$_1$) were identified by selection on MS medium containing 50 mg L$^{-1}$ kanamycin and 200 mg L$^{-1}$ timentin (SmithKline Beecham) and were transferred to soil.

Transformation of tobacco was accomplished using the leaf disk method of Horsch et al. (*Science* 227, 1229, (1985)).

Nitrobenzene Oxidation

For the determination of lignin monomer composition stem tissue was ground to a powder in liquid nitrogen and extracted with 20 mL of 0.1 M sodium phosphate buffer, pH 7.2 at 37° C. for 30 min followed by three extractions with 80% ethanol at 80° C. The tissue was then extracted once with acetone and completely dried. Tissue was saponified by treatment with 1.0 M NaOH at 37° C. for 24 hours, washed three times with water, once with 80% ethanol, once with acetone, and dried. Nitrobenzene oxidation of stem tissue samples was performed with a protocol modified from Iiyamaetal. (*J. Sci. Food Agric.* 51, 481–491, (1990)). Samples of lignocellulosic material (5 mg each) were mixed with 500 L of 2 M NaOH and 25 L of nitrobenzene. This mixture was incubated in a sealed glass tube at 160° C. for 3 h. The reaction products were cooled to room temperature and 5 L of a 20 mg mL$^{-1}$ solution of 3-ethoxy-4-hydroxybenzaldehyde in pyridine was added as an internal standard before the mixture was extracted twice with 1 mL of dichloromethane. The aqueous phase was acidified with HCl (pH 2) and extracted twice with 900 L of ether. The combined ether phases were dried with anhydrous sodium sulfate and the ether was evaporated in a stream of nitrogen. The dried residue was resuspended in 50 L of pyridine, 10 L of BSA (N,O-bis-(trimethylsilyl)-trifluoracetamide) was added and 1 L aliquots of the silylated products were analyzed using a Hewlet-Packard 5890 Series II gas chromatograph equipped with Supelco SPB I column (30 m×0.75 mm). Lignin monomer composition was calculated from the integrated areas of the peaks representing the trimethylsilylated derivatives of vanillin, syringaldehyde, vanillic acid and syringic acid. Total nitrobenzene oxidation-susceptible guaiacyl units (vanillin and vanillic acid) and syringyl units (syringaldehyde and syringic acid) were calculated following correction for recovery efficiencies of each of the products during the extraction procedure relative to the internal standard.

Example One

Identification of the T-DNA Tagged Allele of FAH1

A putatively T-DNA tagged fah1 mutant was identified in a collection of T-DNA tagged lines (Feldman et al., *Mol. Gen. Genet.* 208, 1, (1987)) (Dr. Tim Caspar, Dupont, Wilmington, Del.) by screening adult plants under long wave UV light. A red fluorescent line (line 3590) was selected, and its progeny were assayed for sinapoylmalate content by TLC. The analyses indicated that line 3590 did not accumulate sinapoylmalate. Reciprocal crosses of line 3590 to a fah11-2 homozygote, followed by analysis of the F1 generation for sinapoylmalate content demonstrated that line 3590 was a new allele of fah1, and it was designated fah1-9.

Preliminary experiments indicated co-segregation of the kanamycin-resistant phenotype of the T-DNA tagged mutant with the fah1 phenotype. Selfed seed from 7 kanamycin-resistant [fah1-9×FAH1] F1 plants segregated 1:3 for kanamycin resistance (kan$^{sensitive}$:kan$^{resistant}$) and 3:1 for sinapoylmalate deficiency (Fah1:fah1). From these lines, fah1 plants gave rise to only kan$^{resistant}$,fah1 progeny. To determine the genetic distance between the T-DNA insertion and the FAH1 locus, multiple test crosses were performed between a [fah1-9×FAH1] F1 and a fah1-2 homozygote. The distance between the FAH1 locus and the T-DNA insertion was evaluated by determining the frequency at which FAH1/kan$^{resistant}$ progeny were recovered in the test cross F1. In the absence of crossover events, all kanamycin-resistant F1 progeny would be unable to accumulate sinapoylmalate, and would thus fluoresce red under UV light. In 682 kan$^{resistant}$ F1 progeny examined, no sinapoylmalate proficient plants were identified, indicating a very tight linkage between the T-DNA insertion site and the FAH1 locus.

Example Two

Plasm it Rescue and cDNA Cloning of the FAH1 Gene

Plasmid rescue was conducted using EcoRI-digested DNA prepared from homozygous fah1-9 plants (Behringer et al., Plant Mol. Biol. Rep. 10, 190, (1992)). Five g of EcoRI-digested genomic DNA was incubated with 125 U T4 DNA ligase overnight at 14° C. in a final volume of 1 mL. The ligation mixture was concentrated approximately four fold by two extractions with equal volumes of 2-butanol, and was then ethanol precipitated and electroporated into competent DH5-cells as described (Behringer et al., (1992) supra).

DNA from rescued plasmids was double digested with EcoRI and SalI. Plasmids generated from internal T-DNA sequences were identified by the presence of triplet bands at 3.8, 2.4 and 1.2 kb and were discarded. One plasmid (pCC1) giving rise to the expected 3.8 kb band plus a novel 5.6 kb band was identified as putative external right border plasmid. Using a SacII/EcoRI fragment of pCC1 that appeared to represent Arabidopsis DNA, putative cDNA (pCC30) clones for F5H were identified. The putative F5H clone carried a 1.9 kb SalI-NotI insert, the sequence of which was determined. Blastx analysis (Altschul et al., *J. Mol. Biol.* 215, 403, (1990)) indicated that this cDNA encodes a cytochrome P450-dependent monooxygenase, consistent with earlier reports that (I) the fah1 mutant is defective in F5H (Chapple et al., supra.) and (ii) F5H is a cytochrome P450-dependent monooxygenase (Grand, supra).
Southern and Northern Blot Analysis To determine whether the putative F5H cDNA actually represented the gene that was disrupted in the T-DNA tagged line Southern and northern analysis was used to characterize the available fah1 mutants using the putative F5H cDNA.

Figure 2:
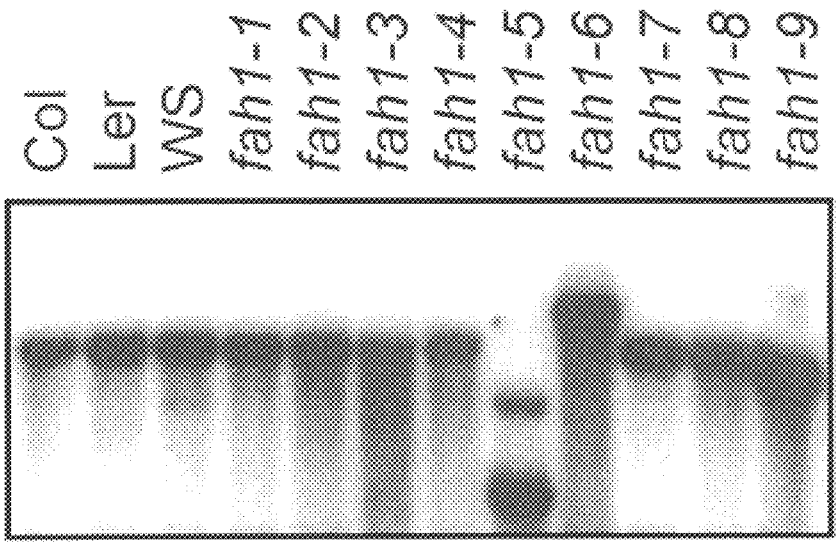
FIG. 2 illustrates a Southern blot analysis comparing hybridization of the F5H cDNA to EcoRI digested genomic DNA isolated from wild type Arabidopsis thaliana and a number of fah1 mutants.

FIG. 2 shows a Southern blot comparing hybridization of the F5H cDNA to EcoRI-digested genomic DNA isolated from wild type (ecotypes Columbia (Col), Landsberg erecta (LER), and Wassilewskija (WS)) and the nine fah1 alleles including the T-DNA tagged fah1-9 allele. WS is the ecotype from which the T-DNA tagged line was generated.

These data indicated the presence of a restriction fragment length polymorphism between the tagged line and the wild type. These data also indicates a restriction fragment length polymorphism in the fah1-8 allele which was generated with fast neutrons, a technique reported to cause deletion mutations.

As shown in FIG. 2, the genomic DNA of the fah1-8 and fah1-9 (the T-DNA tagged line) alleles is disrupted in the region corresponding to the putative F5H cDNA. These date also indicate that F5H is encoded by a single gene in Arabidopsis as expected considering that the mutation in the fah1 mutant segregates as a single Mendelian gene. These data provide the first indication that the putative F5H cDNA corresponds to the gene that is disrupted in the fah1 mutants.

Figure 3:
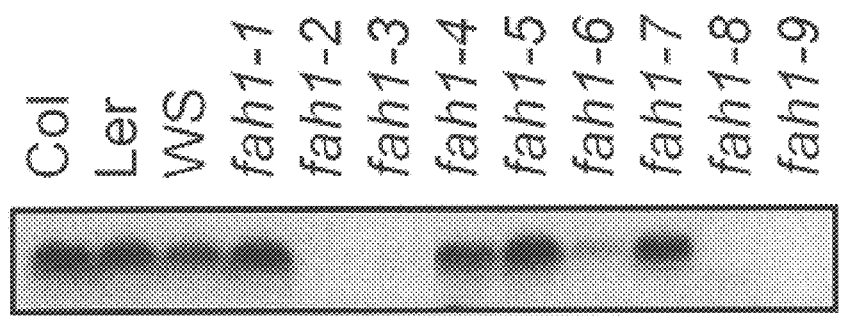
FIG. 3 is a Northern blot analysis comparing hybridization of the F5H cDNA to RNA isolated from wild type Arabidopsis thaliana and a number of fah1 mutants.

Plant material homozygous for nine independently-derived fah1 alleles was surveyed for the abundance of transcript corresponding to the putative F5H cDNA using Northern blot analysis. The data is shown in FIG. 3.

As can be seen from the data, the putative F5H mRNA was represented at similar levels in leaf tissue of Columbia. Landsberg erecta and Wassilewskija ecotypes and in the EMS-induced fah1-1, fah1-4, and fah1-5, as well as the fast neutron-induced fah1-7 Transcript abundance was substantially reduced in leaves from plants homozygous for the fah1-2, fah1-3 and fah1-6, all of which were EMS-induced, the fast neutron-induced mutant fah1-8 and in the tagged line fah1-9. The mRNA a fah1-8 mutant also appears to be truncated. These data provided strong evidence that the cDNA clone that had been identified is encoded by the FAH1 locus.

Example Three

Figure 4:
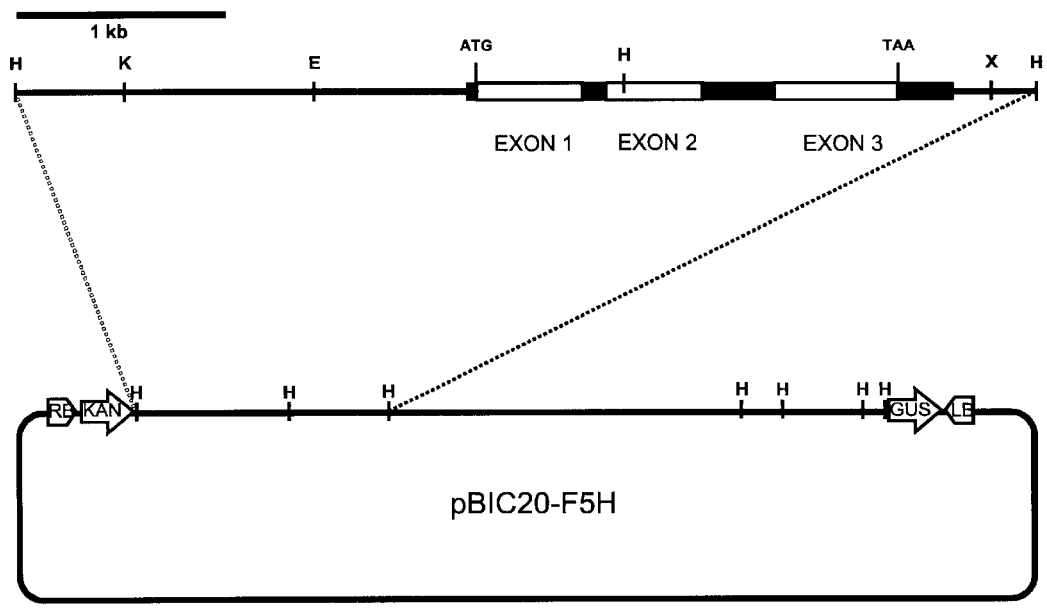
FIG. 4 is an illustration of the pBIC20-F5H cosmid, as well as the F5H overexpression constructs pGA482-35S-F5H and pGA482-C4H-F5H in which the F5H gene is expressed under the control of the constitutive cauliflower mosaic virus 35S promoter, or the Arabidopsis thaliana C4H promoter, respectively.
Figure 4:
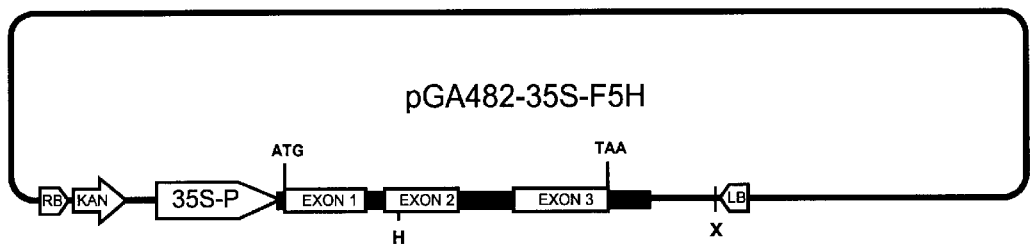
Figure 4:
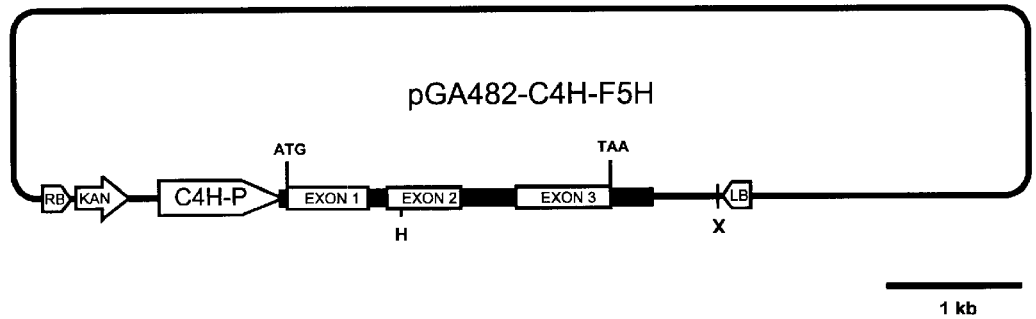
Figure 5:
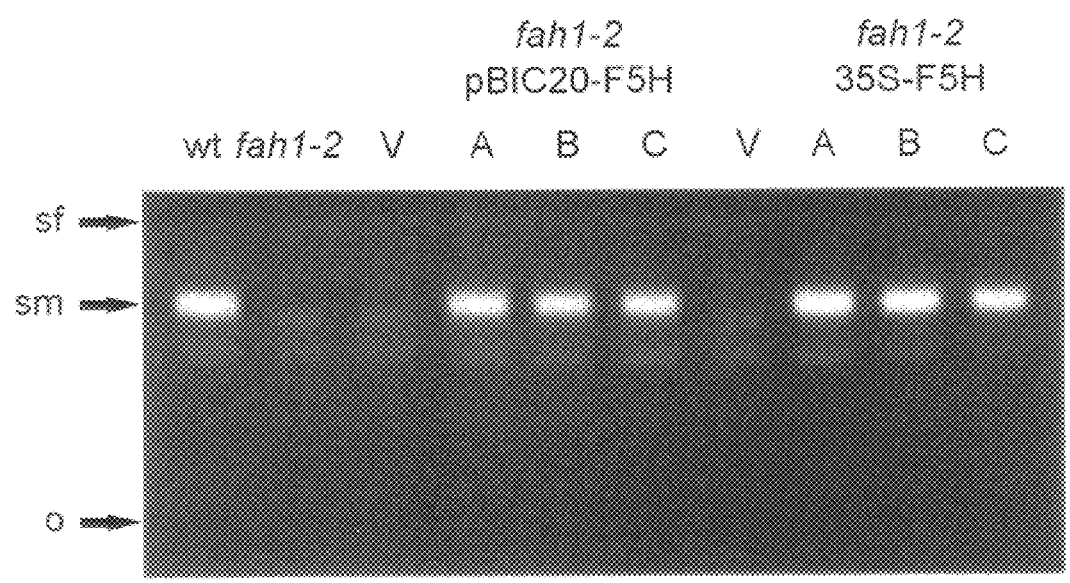
FIG. 5 shows an analysis of sinapic acid-derived secondary metabolites in wild type, the fah1-2 mutant, and independently-derived transgenic fah1-2 plants carrying the T-DNA derived from the pBIC20-F5H cosmid, or the pGA482-35S-F5H overexpression construct.

Demonstration of the Identity of the F5H cDNA by Transformation of fah1 Mutant Plants With Wildtype F5H and Restoration of Sinapoylmalate Accumulation In order to demonstrate the identity of the F5H gene at the functional level, the transformation-competent pBIC20 cosmid library (Meyer et al., supra) was screened for corresponding genomic clones using the full length F5H cDNA as a probe. A clone (pBIC20-F5H) carrying a genomic insert of 17 kb that contains 2.2 kb of sequence upstream of the putative F5H start codon and 12.5 kb of sequence downstream of the stop codon of the F5H gene (FIG. 4) was transformed into the fah1-2 mutant by vacuum infiltration. Thirty independent infiltration experiments were performed and 167 kanamycin-resistant seedlings, representing at least 3 transformants from each infiltration, were transferred to soil and were analyzed with respect to sinapic acid-derived secondary metabolites. Of these plants, 164 accumulated sinapoylmalate in their leaf tissue as determined by TLC (FIG. 5). These complementation data indicate that the gene defective in the fah1 mutant is present on the binary cosmid pBIC20-F5H.

To delimit the region of DNA on the pBIC70-F5H cosmid responsible for complementation of the mutant phenotype, a 2.7 kB fragment of the F5H genomic sequence was fused downstream of the cauliflower mosaic virus 35S promoter in the binary plasmid pGA482 and this construct (pGA482-35S-F5H) (FIG. 4) was transformed into the fah1 mutant. The presence of sinapoyl malate in 109 of 110 transgenic lines analyzed by TLC or by in vivo fluorescence under UV light indicated that the fah1 mutant phenotype had been complemented (FIG. 5). These data provide conclusive evidence that the F5H cDNA has been identified.

Example Four

DNA Sequencing of the F5H cDNA and Genomic Clones

The F5H cDNA and a 5156 bp HindIII-XhoI fragment of the pBIC20-F5H genomic clone were both fully sequenced on both strands and the sequence of the F5H protein (SEQ ID NO.:4) was inferred from the cDNA sequence. The sequence of the *Arabidopsis thaliana* F5H cDNA is given in SEQ ID NO.:2. The sequence of the *Arabidopsis thaliana* F5H genomic clone is given in SEQ ID NO.:3.

Example Five

Identification and DNA Sequencing of the C4H Promoter Sequence

Figure 6:
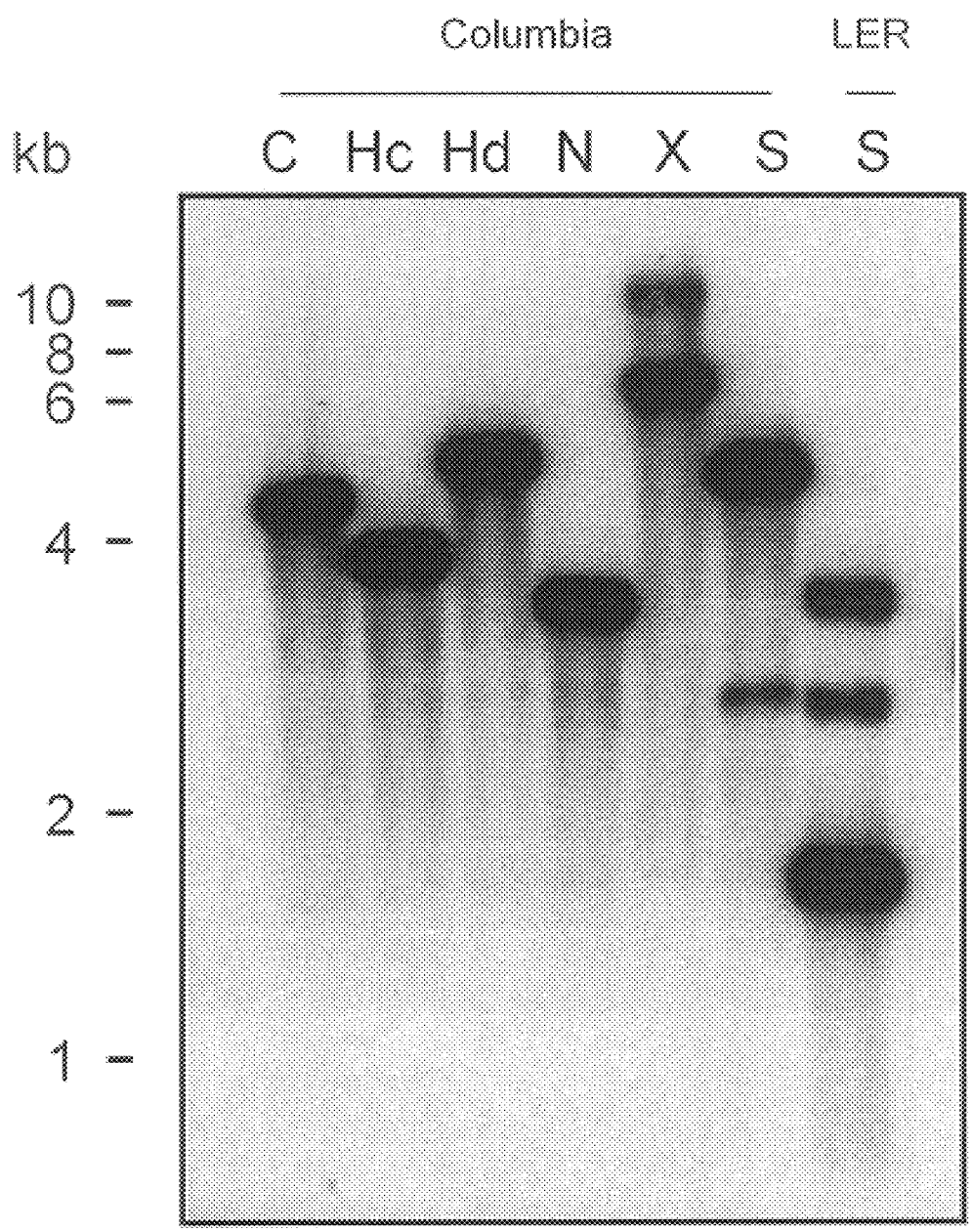
FIG. 6 shows Southern blot analysis of the C4H locus in Arabidopsis. The C4H cDNA was used as a probe against DNA isolated from the Columbia ecotype digested with Csp451, HincII, HindIII, NdeI, and XmaI. DNA from both Columbia and Landsberg erecta ecotypes digested with StyI was included to illustrate the restriction fragment length polymorphism identified with this enzyme.

A search of the Arabidopsis EST library using the keyword "cinnamate" identified a number of clones, most of which corresponded to members of the cytochrome P450 gene superfamily. One of these sequences (clone ID# 126E1T7, Genbank accession number T44874) was highly homologous to C4H sequences characterized from mung bean and Jerusalem artichoke (Mizutani et al., Biochem. Biophys. Res. Commun. 190, 875, (1993); Teutsch et al., Proc. Natl. Acad. Sci. USA 90, 4102, (1993)). This clone also appeared to be a full length P450 cDNA, thus the C4H cDNA EST clone 126E1T7 was obtained from the Ohio State Arabidopsis Resource Center. The putative C4H cDNA was sequenced and was found to be 69 to 72% identical to C4H sequences available in the database and its deduced amino acid sequence shares 84 to 86% identity. To evaluate whether C4H is encoded at a single locus in Arabidopsis, the C4H cDNA was used as a probe against Arabidopsis DNA digested with a number of restriction enzymes (FIG. 6). The probe hybridized to a single band in all lanes except those containing the XmaI and StyI digests, consistent with the presence of sites for these enzymes within the cDNA. Comparison of the hybridization banding pattern obtained with Columbia and Landsberg erecta DNA identified a restriction fragment length polymorphism with StyI. This polymorphism permitted the mapping of the C4H gene to the lower arm of chromosome 2 using recombinant inbred populations (Lister and Dean, Plant J., 4, 745, (1993)). The C4H locus maps to a position 0.8 cM below the marker m283c and 5.1 cM above the marker m323. Further evidence that C4H is encoded by a single gene in Arabidopsis was provided by searching the Arabidopsis thaliana EST database with the full length C4H cDNA sequence. This search retrieved the EST whose sequence is reported here as well as four other sequences (Genbank accession numbers F19837, T04086, N65601, T43776) that are essentially identical to the full length C4H cDNA sequence. The similarity of the C4H cDNA sequence to all others in the database is substantially less after these five are considered. This suggests that there are no other closely related C4H-like genes expressed in Arabidopsis.

Using the C4H cDNA as a probe, a genomic cosmid library was screened to identify a C4H genomic clone from a Landsberg erecta genomic library generated in the binary cosmid vector pBIC20 (Meyer et al., supra). Twelve overlapping genomic clones were isolated that covered the C4H locus, and restriction analysis revealed that these clones fell into three different classes. Southern blot analysis indicated each clone contained a HindIII fragment that carried the entire C4H coding sequence. This 5.4 kb HindIII DNA fragment containing the entire C4H coding sequence from one of the cosmids was subcloned into pGEM-7Zf(+) (Promega) in both the 5'-3' and 3'-5' orientation and transformed into *E. coli* DH5. Alignment of the genomic sequence with the cDNA revealed that the subcloned fragment carried approximately 3 kb of upstream regulatory sequence and that the C4H coding sequence is interrupted by two small introns (intron I, 85 bp; intron II. 220 bp). The sequence of the *Arabidopsis thaliana* C4H genomic DNA is given in SEQ ID NO.:1.

The transcription start site of the C4H gene was determined by primer extension using an oligonucleotide (5'-CCATTATAGTTTGTGTATCCGC-3') (SEQ ID NO:5) complementary to the 5' end of the C4H cDNA clone. This oligonucleotide was end-labeled with [-$^{32}$P]ATP using polynucleotide kinase, and an amount of labeled primer equaling 400,000 cpm was added to 20 g of total RNA isolated from Arabidopsis stems, precipitated and dried. The DNA-RNA hybrids were dissolved in 30 L of hybridization buffer (80% formamide, 1 mM EDTA 0.4 M NaCl. 14 mM PIPES, pH 6.4), incubated at 85 C for 10 min and at 28 C overnight and reprecipitated. The dried pellet was resuspended in 20 L of reverse transcriptase buffer, and the primer was extended using Moloney murine leukemia virus reverse transcriptase (Gibco). The extended product was analyzed by gel electrophoresis adjacent to the products of a sequencing reaction performed with the primer extension oligonucleotide and the C4H genomic clone. The transcription start site for the C4H mRNA was determined to be 86 bp upstream of the initiator ATG. A putative TATA box is found 33 bp upstream of the transcription start site, and a putative CAAT box at -152.

A C4H-GUS transcriptional fusion was constructed using a 2897 bp C4H promoter nested deletion clone carrying the C4H transcription start site. The 3' end of the selected clone terminated at position +34 within the region corresponding to the 5' untranslated region of the C4H cDNA. This fragment was liberated from pGEM-7Zf(+) by digestion with HindIII and ApaI and was subcloned into HindIII-SmaI-digested pBI101 using an ApaI-blunt-ended adaptor. Ligation products were transformed into *E. coli* NM544. The recombinant plasmids were characterized by diagnostic restriction digests prior to use in plant transformation experiments. To evaluate the tissue specificity of C4H promoter-driven GUS expression in transgenic plants, tissues from kanamycin-resistant $T_1$ Arabidopsis plants were incubated in a solution containing 1 mM 5-bromo-4-chloro-3-indolyl--D-glucuronide (X-Gluc), 100 mM sodium phosphate pH 7.0, 10 mM EDTA, 0.5 mM potassium ferricyanide. 0.5 mM potassium ferrocyanide, and 0.1% (v/v) Triton X-100 from 8 to 12 hours at 37 C (Stomp, 1992). Tissues were destained three times in 70% ethanol and whole mounts and sections were analyzed by bright field microscopy.

Figure 7:
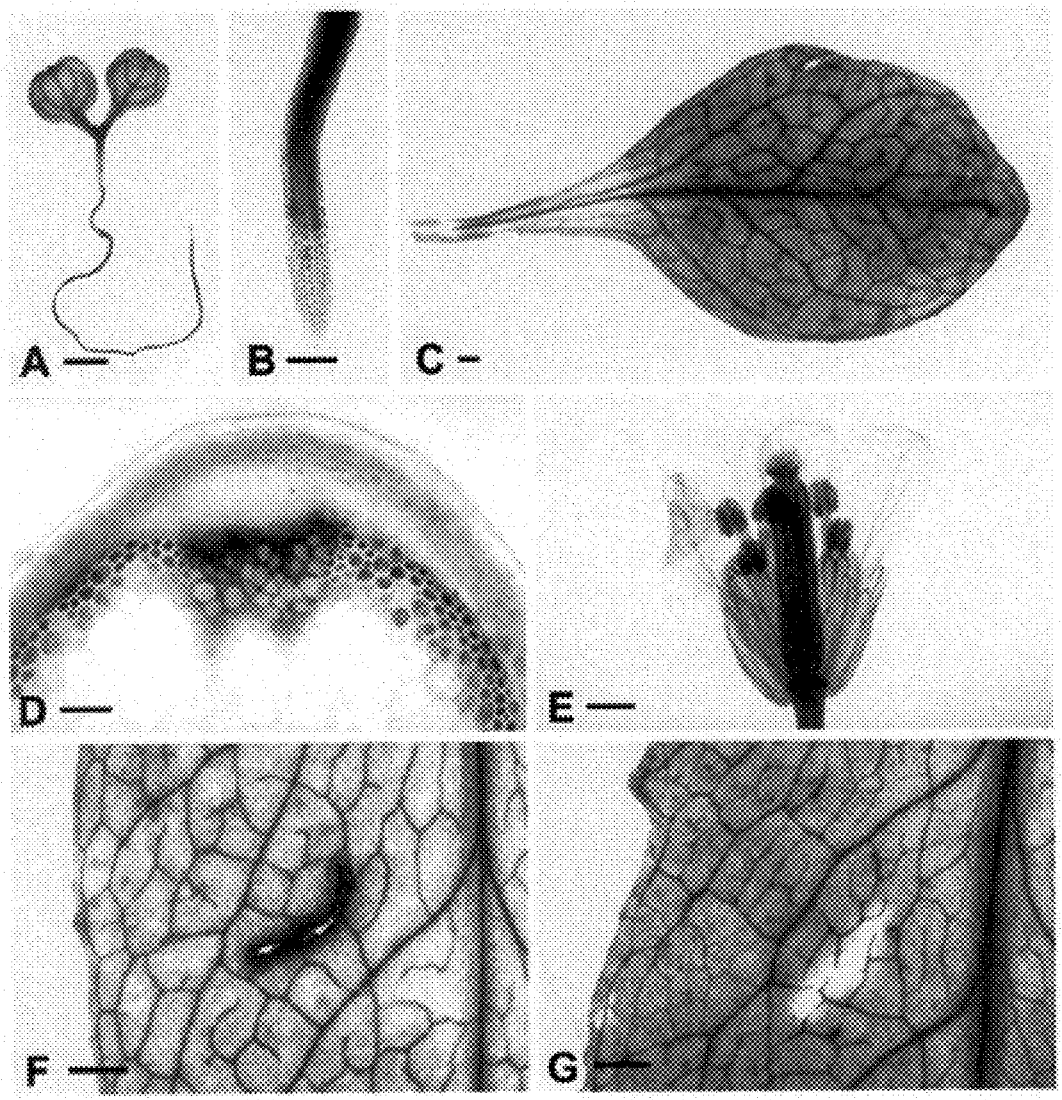
FIG. 7 (Parts A–G) shows in vivo GUS staining in C4H-GUS transformants. A, 10 day-old seedling; B, 10 day-old seedling root; C, mature leaf; D, rachis transverse section; E, flower; F, mature leaf stained 48 hours after wounding: G, mature leaf stained immediately after wounding. A, C, E, F, G. Bar=500 $\mu$m. B, C, Bar=10 $\mu$m.

Among a large number of T1 transformant seedlings carrying the C4H-GUS transcriptional fusion. GUS staining patterns were observed (FIG. 7) that were consistent with RNA blot data obtained using the C4H cDNA probe. In cotyledons. GIFTS staining was diffusely distributed throughout the epidermis and mesophyll with higher levels of staining localized to the vascular tissue and the surrounding parenchyma (FIG. 7). Strong staining was also seen in structures at the cotyledonary margins that resemble hydathodes. In the meristematic region of the seedling, strong GUS activity was present in the developing primary leaves where staining was diffusely distributed, and was not localized to the developing vascular tissue. The highest level of GUS staining in the seedling was observed in the root. This high level of GUS staining was relatively clearly demarcated beginning at the hypocotyl/root junction, and continuing to near the root tip (FIG. 7).

In mature leaves, GUS staining was very strongly localized to the veins (FIG. 7). Similarly, expression of GUS activity in stem cross-sections was restricted to the xylem and the sclerified parenchyma that extends between the vascular bundles (FIG. 7). In reproductive tissues, weak GUS staining was seen throughout the flower including the vasculature of the sepals, with stronger staining evident immediately below the stigmatic surface (FIG. 7).

These data indicate that the Arabidopsis C4H gene has been identified, and that the region of DNA upstream of the C4H coding sequence defines a functional C4H promoter that is capable of directing gene expression in the vascular tissue of transgenic plants.

Example Six

Figure 8:
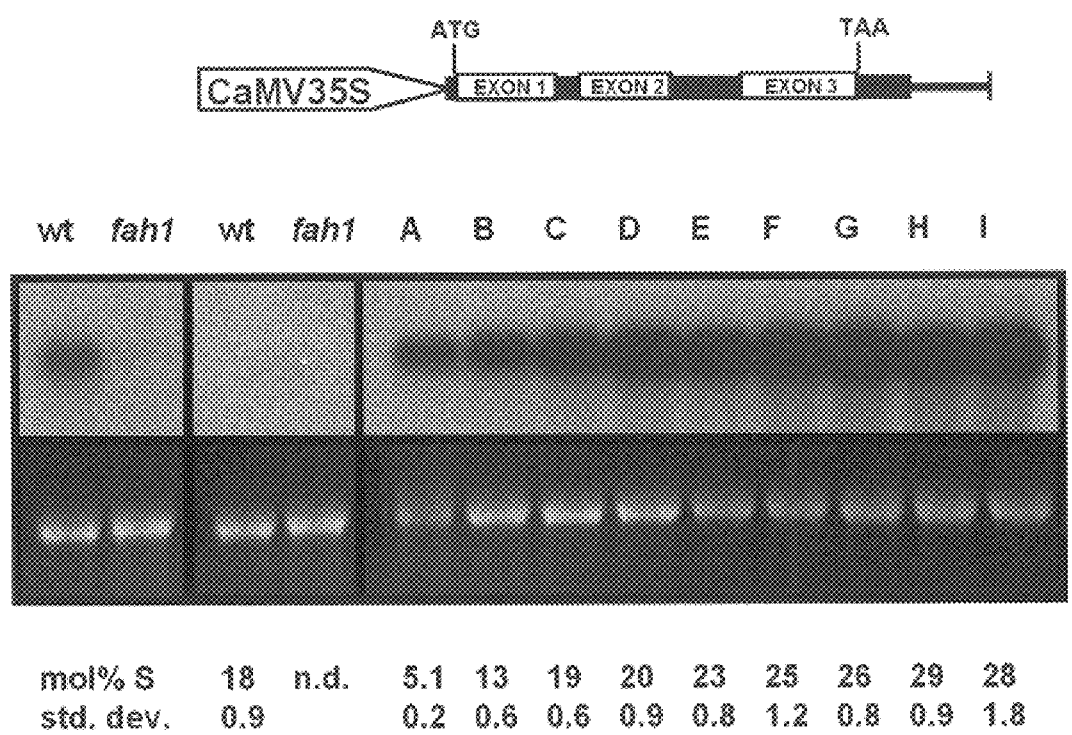
FIG. 8 shows the impact of 35S promoter-drive F5H overexpression on lignin monomer composition. Stem tissues from five week old plants of the wild type, the fah1-2 mutant, and nine independent fah1-2 lines homozygous for the 35S-F5H transgene (top) were harvested and used for RNA isolation and the determination of lignin monomer composition. Blots were probed with the F5H cDNA and were exposed to film for 24 hours to visualize the level of F5H expression in the wild type and the fah1-2 mutant (left panel), and for two hours to evaluate F5H expression in the 35S-F5H transgenics (right panel). Lignin monomer composition of total stem tissue was determined for each line by nitrobenzene oxidation. Average values of ten replicates and their standard deviations are shown (bottom).
Figures 9A, 9B, 9C, 9D:
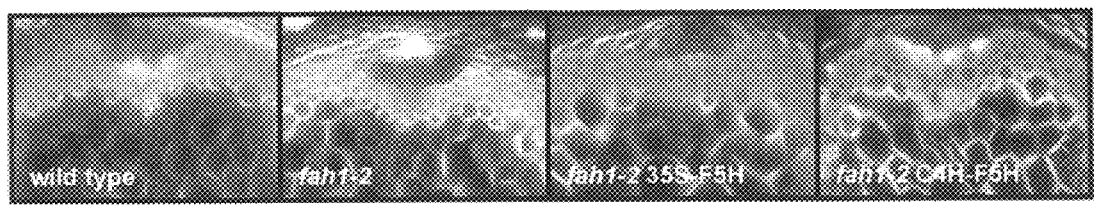
FIG. 9 (Parts A–D) shows histochemical staining of lignin monomer composition in Arabidopsis stem cross sections. Lower rachis segments were hand sectioned, stained with the Mäule reagent and observed by light microscopy using cross-polarizing optics. Red staining indicates the presence of syringyl residues in the plant secondary cell wall.

Modification of Lignin Composition in Plants Transformed with F5H Under the Control of the Cauliflower Mosaic Virus 35S Promoter Arabidopsis plants homozygous for the fah1-2 allele were transformed with Agrobacterium carrying the pGA482-35S-F5H plasmid which contains the chimeric F5H gene under the control of the constitutive cauliflower mosaic virus 35S promoter. Independently homozygous transformants carrying the F5H transgene at a single genetic locus were identified by selection on kanamycin-containing growth media, grown up in soil and plant tissue was analyzed for lignin monomer composition. Nitrobenzene oxidation analysis of the lignin in wild type, fah1-2, and transformants carrying the T-DNA from the pGA482-35S-F5H construct revealed that F5H over-expression as measured by northern blot analysis led to a significant increase in syringyl content of the transgenic lignin (FIG. 8). The lignin of the F5H-over-expressing plants demonstrated a syringl content as high as 29 mol % as opposed to the syringyl content of the wild type lignin which was 18 mol % (Table 1, FIG. 8). In addition, histochemical staining of rachis cross sections indicated that the tissue specificity of syringyl lignin deposition was abolished in transgenic lines ectopically expressing F5H (FIG. 9). Syringyl unit deposition was no longer restricted to the cells of the sclerified parenchyma but was also found in the lignin deposited by the cells of the vascular bundle. This indicates that cells of the vascular bundle are competent to synthesize, secrete and polymerize monolignols derived from sinapic acid if they are made competent to express an active F5H gene. These data clearly demonstrate that over-expression of the F5H gene is useful for the alteration of lignin composition in transgenic plants.

TABLE 1

Impact of 35S Promoter-Driven F5H Expression on Lignin Monomer Composition if Arabidops is

| Line | mol % S |
|---|---|
| wild type | 18.4 +/- 0.91 |
| 88 (A) | 5.06 +/- 0.17 |
| 172 (B) | 13.7 +/- 0.55 |
| 170 (C) | 19.2 +/- 0.56 |
| 122 (D) | 19.9 +/- 0.86 |
| 108 (E) | 22.7 +/- 0.82 |
| 107 (F) | 25.3 +/- 1.23 |
| 180 (G) | 25.8 +/- 0.78 |
| 117 (H) | 28.8 +/- 0.92 |
| 128 (I) | 27.5 +/- 1.80 |

In similar fashion, T1 tobacco (*Nicotiana tabacum*) pGA482 35S-F5H transformants were generated, grown up and analyzed for lignin monomer composition. Nitrobenzene oxidation analysis demonstrated that the syringyl monomer content of the leaf midribs was increased from 14 mol % in the wild type to 40 mol % in the transgenic line that most highly expressed the F5H transgene (Table 2). In contrast, nitrobenzene oxidation analysis of stem tissue demonstrated that in the syringyl lignin content of both wild type and the pGA482 35S-F5H transformants were both approximately 50% (Table 3). These data indicate that the overexpression of F5H directed by the 35S promoter is of limited efficacy in tissues that undergo secondary growth such as tobacco stem. Thus, the pGA482 35S-F5H can be expected to be of limited utility in the modification of lignin monomer composition in trees.

TABLE 2

Impact of 35S Promoter-Driven F5H Expression on Lignin Monomer Composition in Tobacco Leaf Midrib Xylem

| Line | mol % S |
|---|---|
| wild type | 14.3 +/- 1.09 |
| 40 | 22.4 +/- 1.53 |
| 27 | 31.3 +/- 0.50 |
| 48 | 35.7 +/- 6.06 |
| 33 | 40.0 +/- 1.86 |

TABLE 3

Impact of 35S Promoter-Driven F5H Expression on Lignin Monomer Composition in Tobacco Stem Xylem

| Line | mol % S |
|---|---|
| wild type | 49.3 +/- 2.80 |
| 40 | 54.7 +/- 2.20 |
| 27 | 51.2 +/- 1.76 |
| 48 | 52.0 +/- 1.67 |
| 33 | 44.2 +/- 0.15 |

The data in Tables 1 and 2 clearly demonstrate that over-expression of the F5H gene in transgenic plants results in the modification of lignin monomer composition. The transformed plant is reasonably expected to have syringyl lignin monomer content that up to about 35 mol % as measured in whole plant tissue. The data in Table 3, however, indicate that the 35S promoter may be of limited efficacy in the modification of lignin biosynthesis in transgenic plants that undergo secondary growth, and in those plants whose syringyl lignin content naturally exceeds 35%.

Example Seven

Figure 10:
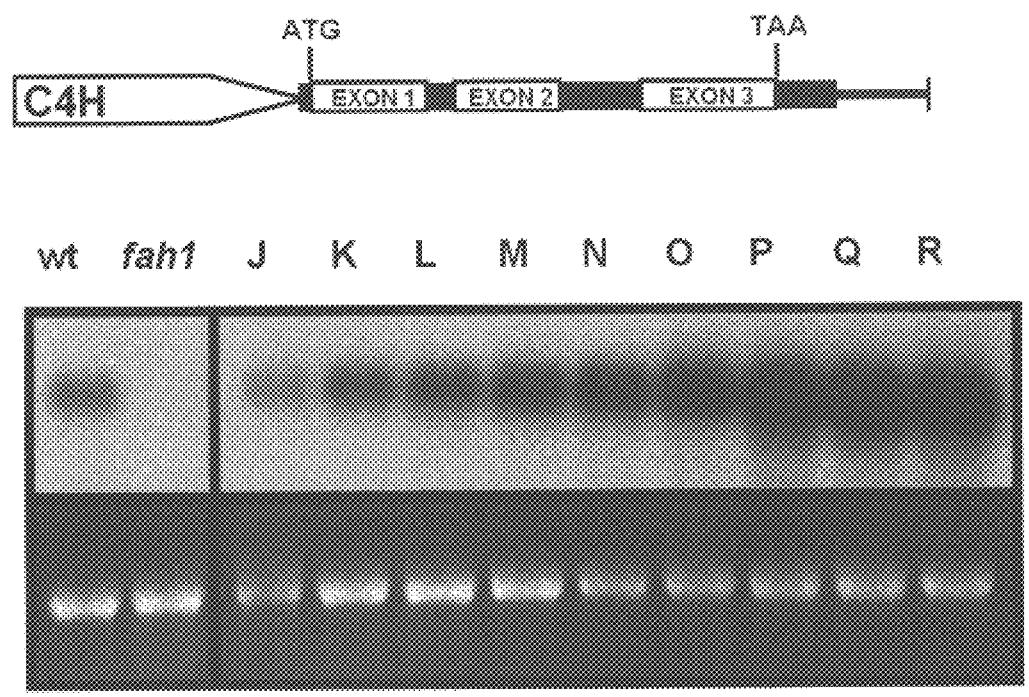
FIG. 10 shows the impact of C4H promoter-driven F5H overexpression on lignin monomer compositions. Stem tissue from five week old plants of the wild type, the fah1-2 mutant, and nine independent fah1-2 lines homozygous for the C4H-F5H transgene (top) were harvested and used for RNA isolation and the determination of lignin monomer composition. Blots were probed with the F5H cDNA and were exposed to film for 12 hours to visualize the level of F5H expression. Lignin monomer composition of total stem tissue was determined for each line by nitrobenzene oxidation. Average values of five replicates and their standard deviations are shown (bottom).
Figure 11:
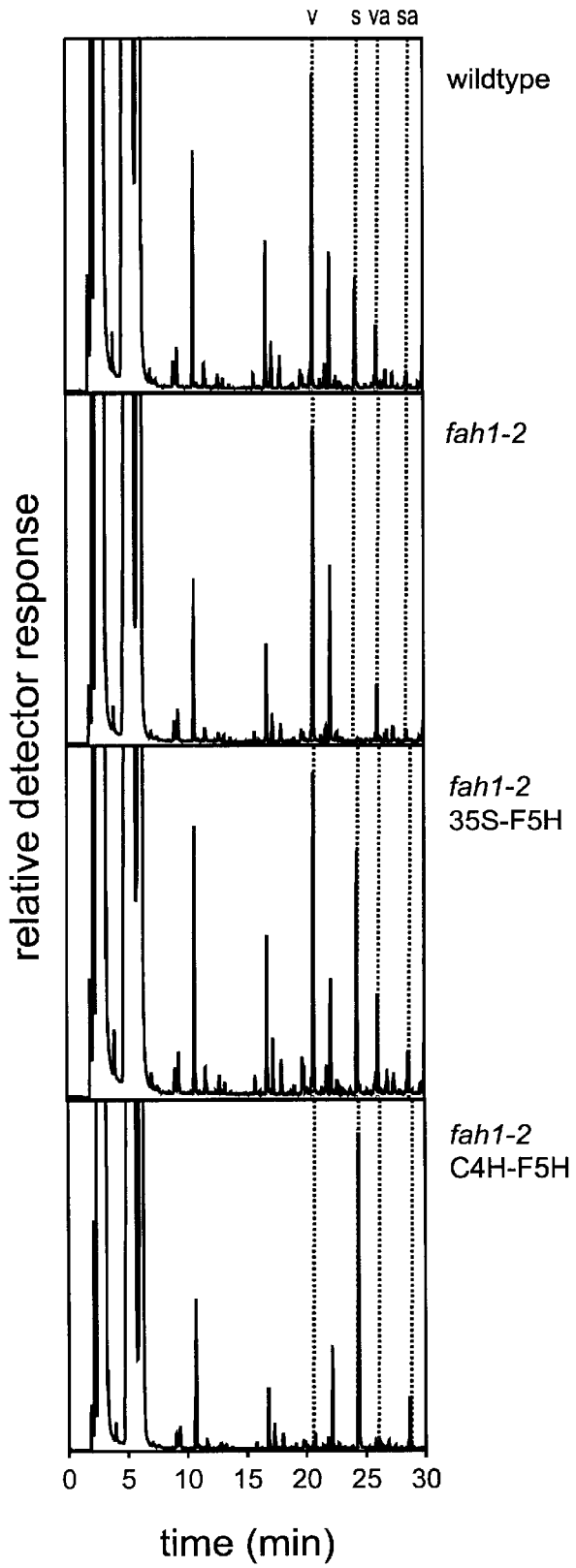
FIG. 11 shows a GC analysis of lignin nitrobenzene oxidation products to illustrate the impact of F5H overexpression on lignin monomer composition in the wild type, the fah1-2 mutant, and the fah1-2 mutant carrying the T-DNA derived from the 35S-F5H overexpression construct, or the C4H-F5H overexpression construct.

Modification of Lignin Composition in Plants Transformed With F5H Under the Control of the C4H Promoter Given the limited efficacy of the pGA482 35S-F5H construct, a new construct was developed in which F5H transcription was driven by regulatory sequences of the C4H gene and this DNA construct was transformed into fah1-2 mutant plants. Lignin analysis of transgenic rachis tissue revealed that expression of F5H under the control of the C4H promoter resulted in the production of a lignin with a syringyl content that greatly exceeded that observed in the 35S-F5H transgenics, despite the fact that the levels of F5H mRNA in these transgenic lines were substantially lower than those in the 35S-F5H transgenics (Table 4, FIGS. 10 and 11). In several of the transgenic lines, the lignin was almost solely comprised of syringyl residues. As in the 35S-F5H transgenics, tissue specificity of syringyl lignin deposition was abolished in plants carrying the C4H-F5H transgene (FIG. 9). When grown under the same controlled conditions, the C4H-F5H transgenic plants were phenotypically indistinguishable from wild type plants.

TABLE 4

Impact of C4H Promoter-Driven F5H Expression on Lignin Monomer Composition in Arabidopsis

| Line | mol % S |
| --- | --- |
| wild type | 19.6 +/− 2.31 |
| 1861 (J) | 44.8 +/− 1.67 |
| 1786 (K) | 47.5 +/− 0.96 |
| 1821 (L) | 70.6 +/− 1.86 |
| 1794 (M) | 77.6 +/− 2.03 |
| 1876 (N) | 82.5 +/− 0.97 |
| 1875 (O) | 85.2 +/− 0.76 |
| 1863 (P) | 90.0 +/− 0.50 |
| 1844 (Q) | 90.1 +/− 0.26 |
| 1824 (R) | 92.1 +/− 0.42 |

Similar analyses of tobacco plants transformed with the pGA482 C4H-F5H construct demonstrated that expression of F5H under the control of the C4H promoter resulted in the production of lignin with a syringyl content that greatly exceeded that observed in the 35S-F5H tobacco transgenics (Table 5). These data indicate that while the 35S-F5H construct leads to an increase in syringyl monomer content in the lignin of leaves, the construct has little utility in woody tissues such as tobacco stem. In contrast, the C4H-F5H overexpression construct shows a greater efficacy in tobacco stems, and thus provides the ability to modify the lignin monomer composition of other woody species. It should be noted that as in the case of the Arabidopsis C4H-F5H transgenics, the C4H-F5H transgenic plants were phenotypically indistinguishable from wild type plants.

TABLE 5

Impact of C4H Promoter-Driven F5H Expression on Lignin Monomer Composition in Tobacco Stem Xylem

| Line | mol % S |
| --- | --- |
| wild type | 50.1 +/− 1.40 |
| 37 | 48.1 +/− 1.67 |
| 2 | 63.7 +/− 1.99 |
| 32 | 71.9 +/− 1.35 |
| 9 | 78.4 +/− 1.64 |
| 8 | 79.4 +/− 0.57 |
| 18 | 79.6 +/− 1.91 |
| 35 | 84.2 +/− 0.76 |

These results demonstrate that the composition of the lignin polymer is dictated by the temporal and tissue-specific expression pattern of F5H in Arabidopsis and tobacco. It has further been shown that the CaMV 35S promoter, which frequently has been used in transgenic studies aimed at the modification of lignin biosynthesis, fails to promote F5H gene expression in cells undergoing or providing precursors for lignification. The promoter of the C4H gene used in this study is far more efficient in this regard and will be a very valuable tool in transgenic studies addressing plant lignification in the future. These data also indicate that the use of other endogenous promoters in biotechnological applications may enhance not only tissue-specificity but also tissue-efficacy of transgene expression when compared to non-specific ectopic promoters such as the CaMV 35S promoter. Finally, it is shown herein that it is possible to genetically engineer plants to accumulate lignin that is highly enriched in syringyl residues. The unaltered morphology of tracheary elements and sclerified parenchyma in transgenic plants made in accordance with the invention suggests that this lignin still provides lignified cells with sufficient rigidity to function normally in water conduction and mechanical support.

What is claimed is:

1. An isolated promoter effective for controlling expression of a coding sequence, comprising a nucleotide sequence selected from the group consisting of an isolated Arabidopsis C4H promoter of SEQ ID NO:1, a part of an isolated Arabidopsis C4H promoter of SEQ ID NO: 1 effective to control expression of a coding sequence, and a nucleotide sequence which will hybridize thereto under moderately stringent hybridization conditions and which is effective to control expression of a coding sequence.

2. An isolated DNA construct comprising the promoter of claim 1 operably linked to a coding sequence.

3. The promoter of claim 1, comprising a nucleotide sequence selected from the group consisting of SEQ ID NO:1 and a part of SEQ ID NO: 1 effective to control expression of a coding sequence.

4. The construct according to claim 2, which is stably integrated within a plant's genomic DNA.

5. The construct according to claim 2 wherein the promoter regulates expression of the coding sequence in a host plant cell; and wherein the host plant cell expresses the coding sequence.

6. The construct according to claim 2, wherein the coding sequence encodes a ferulate-5-hydroxylase (F5H) enzyme.

7. The DNA construct according to claim 2, wherein the coding sequence comprises a sequence selected from the group consisting of the sequence of SEQ ID NO: 2 and the sequence of SEQ ID NO: 3.

8. The DNA construct according to claim 2, wherein the coding sequence is operably linked in either sense or antisense orientation to the promoter.

9. A vector comprising the DNA construct according to claim 2.

10. The DNA construct according to claim 2, wherein the coding sequence encodes an enzyme that functions in a plant cell to alter the syringyl:guaiacyl lignin monomer ratios in the plant cell, and wherein the coding sequence comprises a polynucleotide having a sequence selected from the group consisting of the sequence set forth in SEQ ID NO:2, the sequence set forth in SEQ ID NO:3 and a sequence which will hybridize thereto under moderately stringent hybridization conditions.

11. A plant transformed with the vector of claim 9, or progeny thereof, the plant being capable of expressing the coding sequence.

12. The transformed plant of claim 11 wherein the host plant is selected from the group consisting of alfalfa (Medicago sp.), rice (Oryza sp.), maize (*Zea mays*), oil seed rape (Brassica sp.), forage grasses, tobacco (Nicotiana sp.), eucalyptus (Eucalyptus sp.), pine (Pinus sp.), spruce (Picea sp.), poplar (Populus sp.) and (Arabidopsis sp.).

13. The transformed plant of claim 11 wherein the host plant is a tree crop.

14. A method of expressing a foreign DNA sequence in a plant, comprising:

operatively linking a foreign DNA sequence to a promoter effective for controlling expression of the foreign DNA sequence to provide an expression construct; and transforming the plant with the expression construct to provide a transformed plant, wherein the transformed plant expresses the foreign DNA in the plant;

wherein the promoter comprises a nucleotide sequence selected from the group consisting of the isolated Arabidopsis C4H promoter of SEQ ID NO:1, a part of the isolated Arabidopsis C4H promoter of SEQ ID NO: 1 effective to control expression of the foreign DNA sequence, and a nucleotide sequence which will hybridize thereto under moderately stringent hybridization conditions and which is effective to control expression of the foreign DNA sequence.

15. A transgenic plant obtained according to the method of claim 14 or progeny thereof.

16. The method of claim 14, wherein said transforming comprises:

(i) transforming a cell, tissue or organ from a host plant with the expression construct;

(ii) selecting a transformed cell, cell callus, somatic embryo, or seed which contains the expression construct;

(iii) regenerating a whole plant from the selected transformed cell, cell callus, somatic embryo, or seed; and (iv) selecting a regenerated whole plant that expresses the foreign DNA sequence.

17. The method of claim 14, wherein the foreign DNA sequence encodes an enzyme that functions in a plant cell to alter the syringyl:guaiacyl lignin monomer ratios in the plant cell, and wherein the DNA sequence comprises a polynucleotide having a sequence selected from the group consisting of the sequence set forth in SEQ ID NO:2, the sequence set forth in SEQ ID NO:3 and a sequence which will hybridize thereto under moderately stringent hybridization conditions.

18. The method of claim 14, wherein the foreign DNA sequence comprises a polynucleotide that functions in the plant to cause altered syringyl:guaiacyl lignin monomer ratios in the plant, the polynucleotide having a sequence selected from the group consisting of the sequence set forth in SEQ ID NO:2, the sequence set forth in SEQ ID NO:3 and a sequence which will hybridize thereto under moderately stringent hybridization conditions.

* * * * *

SEQUENCE LISTING

<160> NUMBER OF SEQ ID NOS: 5

<210> SEQ ID NO 1
<211> LENGTH: 5432
<212> TYPE: DNA
<213> ORGANISM: Arabidopsis thaliana

<400> SEQUENCE: 1

```
aagcttagag gagaaactga gaaaatcagc gtaatgagag acgagagcaa tgtgctaaga       60
gaagagattg ggaagagaga agagacgata aaggaaacgg aaaagcatat ggaggagctt      120
catatggagc aagtgaggct gagaagacgg tcgagtgagc ttacggaaga agtggaaagg      180
acgagagtgt ctgcatcgga aatggctgag cagaaaagag aagctataag acagctttgt      240
atgtctcttg accattacag agatgggtac gacaggcttt ggagagttgt tgccggccat      300
aagagtaaga gagtagtggt tttaacaact tgaagtgtaa gaacaatgag tcaatgacta      360
cgtgcaggac attggacata ccgtgtgttc ttttggattg aaatgttgtt tcgaagggct      420
gttagttgat gttgaaaata ggttgaagtt gaataatgca tgttgatata gtaaatatca      480
atggtaatat tttctcattt cccaaaactc aaatgatatc atttaattat aaactaacgt      540
```

-continued

```
aaactgttga caatacactt atggttaaaa atttggagtc ttgttttagt atacgtatca      600
ccaccgcacg gtttcaaaac cacataattg taaatgttat tggaaaaaag aacccgcaat      660
acgtattgta ttttggtaaa catagctcta agcctctaat atataagctc tcaacaattc      720
tggctaatgg tcccaagtaa gaaaagccca tgtattgtaa ggtcatgatc tcaaaaacga      780
gggtgaggtg gaatactaac atgaggagaa agtaaggtga caaattttg gggcaatagt       840 ggtggatatg gtggggaggt aggtagcatc atttctccaa gtcgctgtct ttcgtggtaa      900
tggtaggtgt gtctctcttt atattattta ttactactca ttgttaattt cttttttct       960 acaatttgtt tcttactcca aaatacgtca caaatataat actaggcaaa taattattta     1020
attgtaagtc aatagagtgg ttgttgtaaa attgattttt gatattgaaa gagttcatgg     1080
acggatgtgt atgcgccaaa tgctaagccc ttgtagtctt gtactgtgcc gcgcgtatat     1140
tttaaccacc actagttgtt tctctttttc aaaaacacac aaaaaataat ttgttttcgt     1200
aacggcgtca aatctgacgg cgtctcaata cgttcaattt tttctttctt tcacatggtt     1260
tctcatagct ttgcattgac cataggtaaa gggataagga taaaggtttt ttctcttgtt     1320
tgttttatcc ttattattca aaatggataa aaaaacagtc ttattttgat ttctttgatt     1380 aaaaagtca ttgaaattca tatttgattt tttgctaaat gtcaactcag agacacaaac      1440
gtaatgcact gtcgccaata ttcatggatc atgaccatga atatcactag aataattgaa     1500
aatcagtaaa atgcaaacaa agcatttttct aattaaaaca gtcttctaca ttcacttaat    1560
tggaatttcc tttatcaaac ccaaagtcca aaacaatcgg caatgttttg caaaatgttc     1620
aaaactattg gcgggttggt ctatccgaat tgaagatctt ttctccatat gatagaccaa     1680
cgaaattcgg catacgtgtt ttttttttg ttttgaaaac cctttaaaca accttaattc      1740
aaaatactaa tgtaaccttta ttgaacgtgc atctaaaaat tttgaacttt gcttttgaga    1800
aataatcaat gtaccaataa agaagatgta gtacatacat tataattaaa tacaaaaaag    1860
gaatcaccat atagtacatg gtagacaatg aaaaacttta aaacatatac aatcaataat    1920
actctttgtg cataactttt tttgtcgtct cgagtttata tttgagtact tatacaaact     1980
attagattac aaactgtgct cagatacatt aagttaatct tatatacaag agcactcgag     2040
tgttgtcctt aagttaatct taagatatct tgaggtaaat agaaatagtt aactcgttttt    2100 tattttcttt ttttttaccat gagcaaaaaa agatgaagta agttcaaaac gtgacgaatc   2160
tacatgttac tacttagtat gtgtcaatca ttaaatcggg aaaacttcat catttcagga     2220
gtactacaaa actcctaaga gtgagaacga ctacatagta catattttga taaaagactt     2280
gaaaacttgc taaaacgaat ttgcgaaaat ataatcatac aagtagaacc actgatttga    2340
tcgaattatt catagctttg taggatgaac ttaactaaat aatatctcac aaaagtattg     2400 acagtaaccta gtactatac tatctatgtt agaatatgat tatgatataa tttatccccct   2460 cacttattca tatgattttt gaagcaacta ctttcgtttt tttaacattt tctttttgg     2520 ttttgttaa tgaacatatt tagtcgtttc ttaattccac tcaaatagaa aatacaaaga    2580
gaactttatt taatagatat gaacataatc tcacatcctc ctcctacctt caccaaacac    2640
ttttacatac actttgtggt ctttcttttac ctaccaccat caacaacaac accaagcccc   2700
actcacacac acgcaatcac gttaaatcta acgccgttta ttatctcatc attcaccaac    2760
tcccacgtac ctaacgccgt ttaccttttg ccgttggtcc tcatttctca aaccaaccaa    2820
acctctccct cttataaaat cctctctccc ttctttattt cttcctcagc agcttcttct    2880
gctttcaatt actctcgccg acgattttct caccggaaaa aaacaatatc attgcggata    2940
```

```
cacaaactat aatggacctc ctcttgctgg agaagtctct aatcgccgtc ttcgtggcgg   3000
tgattctcgc cacggtgatt tcaaagctcc gcggcaagaa attgaagcta cctccaggtc   3060
ctataccaat tccgatcttc ggaaactggc ttcaagtagg agatgatctc aaccaccgta   3120
atctcgtcga ttacgctaag aaattcggcg atctcttcct cctccgtatg ggtcagcgta   3180
acctagtcgt cgtctcttca ccggatctaa ccaaggaagt gctccacaca caaggcgttg   3240
agtttggatc tagaacgaga aacgtcgtgt tcgacatttt caccgggaaa ggtcaagata   3300
tggtgttcac tgtttacggc gagcattgga ggaagatgag aagaatcatg acggttcctt   3360
tcttcaccaa caaagttgtt caacagaatc gtgaaggttg ggagtttgaa gcagctagtg   3420
ttgttgaaga tgttaagaag aatccagatt ctgctacgaa aggaatcgtg ttgaggaaac   3480
gtttgcaatt gatgatgtat aacaatatgt tccgtatcat gttcgataga agatttgaga   3540
gtgaggatga tcctcttttc cttaggctta aggctttgaa tggtgagaga agtcgattag   3600
ctcagagctt tgagtataac tatggagatt tcattcctat ccttagacca ttcctcagag   3660
gctatttgaa gatttgtcaa gatgtgaaag atcgaagaat cgctcttttc aagaagtact   3720
ttgttgatga gaggaagtga gttcattttt ttgtttctat ttttagtttt atcttttgag   3780
tttgcttttg ggaaattgac attgatgatt cattcttaca ggcaaattgc gagttctaag   3840
cctacaggta gtgaaggatt gaaatgtgcc attgatcaca tccttgaagc tgagcagaag   3900
ggagaaatca acgaggacaa tgttctttac atcgtcgaga acatcaatgt cgccggtaac   3960
ttctatttct tacttgtagg atacgtaatc aatcctctag acgtctctgc ttgcataagg   4020
aattggacat tagtgtttta agtgaatcct agaaatccgg aattgtaacc ataacaggaa   4080
attaggctca tgtaggttgg ttttttggtc tcccctgaag aggctggatt gtatatggtt   4140
ttgtgaagct gatatcttga tttctgctga acagcgatt gagacaacat tgtggtctat   4200
cgagtgggga attgcagagc tagtgaacca tcctgaaatc cagagtaagc taaggaacga   4260
actcgacacg gttcttggac cgggtgtgca agtcaccgag cctgatcttc acaaacttcc   4320
ataccttcaa gctgtggtta aggagactct tcgtctgaga atggcgattc ctctcctcgt   4380
gcctcacatg aacctccatg atgcgaagct cgctggctac gatatcccag cagaaagcaa   4440
aatccttgtt aatgcttggt ggctagcaaa caaccccaac agctggaaga agcctgaaga   4500
gtttagacca gagaggttct ttgaagaaga atcgcacgtg gaagctaacg gaaatgactt   4560
caggtatgtg ccgtttggtg ttggacgtag aagctgtccc gggattatat tggcattacc   4620
tattttgggg atcaccattg gtaggatggt ccagaacttc gagcttcttc ctcctccagg   4680
acagtctaaa gtggatacta gtgagaaagg tggacaattg agcttgcaca tccttaacca   4740
ctccataatc gttatgaaac caaggaactg ttaaactttc tgcacaaaaa aaaggatgaa   4800 gatgactta taaatgttg tgaaatctgt tgaaatattc ccttgttttg cttttgtgag   4860 atgttttgt gtaaaatgtc tttaaatggt tcgttctacg attgcaataa taattagtgg   4920
tgctcattct tttggatgga tcgatgttat acttatatca tttgaaaatc tcatgattgt   4980
tggacttgga ccatagttgt taatttgaag gtttctaggt tctaacgtta ataatcttgt   5040
tcacaccaaa taaatctcat tacacaattt ggggaggtat taaagatta ccaaaatagg   5100 ttaattacaa attcgactat ttccagtaat atgggctaat ataggctcca atttagatac   5160
taataatggg ctttataaag cccatttgtt tttctcctta atatcatcac tcgcagagat   5220
tacgcagcgg gaatatataaa acaccaaatg cttacaagaa attttcgaaa tttgaaagac   5280
```

| | |
|---|---:|
| cgttcgtttc gttgtctttg atttccctg ctgcaaattt gatcaaagat catcggattc | 5340 |
| atcattcggt agcagcaatt atcatgttct cgtaatcgtt tctatgctcc gagctccgtt | 5400 |
| ttggggacgc gattcagata ctgtcgaagc tt | 5432 |

<210> SEQ ID NO 2
<211> LENGTH: 1838
<212> TYPE: DNA
<213> ORGANISM: Arabidopsis thaliana

<400> SEQUENCE: 2

| | |
|---|---:|
| aaaaaaaaca ctcaatatgg agtcttctat atcacaaaca ctaagcaaac tatcagatcc | 60 |
| cacgacgtct cttgtcatcg ttgtctctct tttcatcttc atcagcttca tcacacggcg | 120 |
| gcgaaggcct ccatatcctc ccggtccacg aggttggccc atcataggca acatgttaat | 180 |
| gatggaccaa ctcacccacc gtggtttagc caatttagct aaaaagtatg gcggattgtg | 240 |
| ccatctccgc atgggattcc tccatatgta cgctgtctca tcacccgagg tggctcgaca | 300 |
| agtccttcaa gtccaagaca gcgtcttctc gaaccggcct gcaactatag ctataagcta | 360 |
| tctgacttac gaccgagcgg acatggcttt cgctcactac ggaccgtttt ggagacagat | 420 |
| gagaaaagtg tgtgtcatga aggtgtttag ccgtaaaaga gctgagtcat gggcttcagt | 480 |
| tcgtgatgaa gtggacaaaa tggtccggtc ggtctcttgt aacgttggta agcctataaa | 540 |
| cgtcggggag caaattttg cactgacccg caacataact taccgggcag cgtttgggtc | 600 |
| agcctgcgag aagggacaag acgagttcat aagaatctta caagagttct ctaagctttt | 660 |
| tggagccttc aacgtagcgg atttcatacc atatttcggg tggatcgatc cgcaagggat | 720 |
| aaacaagcgg ctcgtgaagg cccgtaatga tctagacgga tttattgacg atattatcga | 780 |
| tgaacatatg aagaagaagg agaatcaaaa cgctgtggat gatggggatg ttgtcgatac | 840 |
| cgatatggtt gatgatcttc ttgcttttta cagtgaagag gccaaattag tcagtgagac | 900 |
| agcggatctt caaaattcca tcaaacttac ccgtgacaat atcaaagcaa tcatcatgga | 960 |
| cgttatgttt ggaggaacgg aaacggtagc gtcggcgata gagtgggcct taacggagtt | 1020 |
| attacggagc cccgaggatc taaaacgggt ccaacaagaa ctcgccgaag tcgttggact | 1080 |
| tgacagacga gttgaagaat ccgacatcga aagttgact tatctcaaat gcacactcaa | 1140 |
| agaaacccta aggatgcacc caccgatccc tctcctcctc cacgaaaccg cggaggacac | 1200 |
| tagtatcgac ggtttcttca ttcccaagaa atctcgtgtg atgatcaacg cgtttgccat | 1260 |
| aggacgcgac ccaacctctt ggactgaccc ggacacgttt agaccatcga ggttttttgga | 1320 |
| accgggcgta ccggatttca aagggagcaa tttcgagttt ataccgttcg ggtcgggtcg | 1380 |
| tagatcgtgc ccgggtatgc aactagggtt atacgcgctt gacttagccg tggctcatat | 1440 |
| attacattgc ttcacgtgga aattacctga tgggatgaaa ccaagtgagc tcgacatgaa | 1500 |
| tgatgtgttt ggtctcacgg ctcctaaagc cacgcggctt ttcgccgtgc caaccacgcg | 1560 |
| cctcatctgt gctctttaag tttatggttc gagtcacgtg gcaggggttt tggtatggtg | 1620 |
| aaaactgaaa agtttgaagt tgccctcatc gaggatttgt ggatgtcata tgtatgtatg | 1680 |
| tgtatacacg tgtgttctga tgaaaacaga tttggctctt tgtttgccct ttttttttt | 1740 |
| ttctttaatg gggatttttcc ttgaatgaaa tgtaacagta aaaataagat ttttttcaat | 1800 |
| aagtaattta gcatgttgca aaaaaaaaaa aaaaaaa | 1838 |

<210> SEQ ID NO 3
<211> LENGTH: 5156

```
<212> TYPE: DNA
<213> ORGANISM: Arabidopsis thaliana

<400> SEQUENCE: 3
aagcttatgt atttccttat aaccatttta ttctgtatat aggggacag  aaacataata      60
agtaacaaat agtggtttta ttttttttaaa tatacaaaaa ctgtttaacc attttatttc    120
ttggttagca aaattttgat atattcttaa gaaactaata ttttaggttg atatattgca    180
gtcactaaat agttttaaaa gacacgaagt tggtaagaac aggcatatat tattcgattt    240
aattaggaat gcttatgtta atctgattcg actaattaga aacgacgata ctatgagctc    300
atagatggtc ccacgaccca ctctcccatt tgatcaatat tcaactgagc aatgaaacta    360
attaaaaacg tggttagatt aaaaaaataa attgtgcagg tagcggatat ataatactag    420
tagggggttaa aaataaaata aaacaccaca gtattaaatt tttgtttcaa agtattatc     480
aatagttttt ttgcttcaaa aatatcacaa attttttgtat gaaatatttc tttaacgaaa    540
ataaattaaa taaaatttaa aatttatatt tggagttcta tttttaattt agagttttta    600
ttgttaccac atttttgaa ttattctaat attaatttgt gatattatta caaaagtaa      660
aaatatgata ttttagaata ctattatcga tatttgatat tattgacctt agctttgttt    720
gggtggagac atgtgattat cttattacct ttttattcca tgaaactaca gagttcgcca    780
ggtaccatac atgcacacac cctcgtgaag ccgtgactta atatgatcta gaacttaaat    840
agtactacta attgtgtcat ttgaactttc tcctatgtcg gtttcacttc atgtatcgca    900
gaacaggtgg aatacagtgt ccttgagttt cacccaaatc ggtccaattt tgtgatatat    960
attgcgatac agacatacag cctacagagt tttgtcttag cccactggtt ggcaaacgaa   1020
attgtcttta ttttttttatg ttttgttgtc aatgtgtctt tgttttttaac tagattgagg   1080
tttaattttta atacattttgt tagtttacag attatgcagt gtaatctgat aatgtaagtt   1140
gaactgcgtt ggtcaaagtc ttgtgtaacg cactgtatct aaattgtgag taacgacaaa   1200
ataattaaaa ttaaaggacc ttcaagtatt attagtatct ctgtctaaga tgcacaggta   1260
ttcagtaata gtaataaata attacttgta taattaatat ctaattagta aaccttgtgt   1320
ctaaacctaa atgagcataa atccaaaagc aaaaatctaa acctaactga aaaagtcatt   1380
acgaaaaaaa gaaaaaaaaa agagaaaaaa ctacctgaaa agtcatgcac aacgttcatc   1440
ttggctaaat ttatttagtt tattaaatac aaaaatggcg agtttctgga gtttgttgaa   1500
aatatatttg tttagccact ttagaatttc ttgttttaat ttgttattaa gatatatcga   1560
gataatgcgt ttatatcacc aatattttg ccaaactagt cctatacagt cattttttcaa   1620
cagctatgtt cactaatttta aaacccactg aaagtcaatc atgattcgtc atatttatat   1680
gctcgaattc agtaaaatcc gtttggtata ctatttattt cgtataagta tgtaattcca   1740
ctagatttcc ttaaactaaa ttatatattt acataattgt tttctttaaa agtctacaac   1800
agttattaag ttataggaaa ttatttcttt tatttttttt tttttttagg aaattatttc   1860
ttttgcaaca catttgtcgt ttgcaaactt ttaaagaaa  ataaatgatt gttataattg   1920
attacatttc agtttatgac agattttttt tatctaacct ttaatgtttg tttccctgtt   1980
tttaggaaaa tcataccaaa atatatttgt gatcacagta aatcacggaa tagttatgac   2040
caagattttc aaagtaatac ttagaatcct attaaataaa cgaaatttta ggaagaaata   2100
atcaagattt taggaaacga tttgagcaag gatttagaag atttgaatct ttaattaaat   2160
attttcattc ctaaataatt aatgctagtg gcataatatt gtaaataagt tcaagtacat   2220
```

```
gattaatttg ttaaaatggt tgaaaaatat atatatgtag attttttcaa aaggtatact    2280
aattattttc atattttcaa gaaaatataa gaaatggtgt gtacatatat ggatgaagaa    2340
atttaagtag ataatacaaa aatgtcaaaa aaagggacca cacaatttga ttataaaacc    2400
tacctctcta atcacatccc aaaatggaga actttgcctc ctgacaacat ttcagaaaat    2460
aatcgaatcc aaaaaaaaca ctcaatatgg agtcttctat atcacaaaca ctaagcaaac    2520
tatcagatcc cacgacgtct cttgtcatcg ttgtctctct tttcatcttc atcagcttca    2580
tcacacggcg gcgaaggcct ccatatcctc ccggtccacg aggttggccc atcataggca    2640
acatgttaat gatggaccaa ctcacccacc gtggtttagc caatttagct aaaaagtatg    2700
gcggattgtg ccatctccgc atgggattcc tccatatgta cgctgtctca tcacccgagg    2760
tggctcgaca agtccttcaa gtccaagaca gcgtcttctc gaaccggcct gcaactatag    2820
ctataagcta tctgacttac gaccgagcgg acatggcttt cgctcactac ggaccgtttt    2880
ggagacagat gagaaaagtg tgtgtcatga aggtgtttag ccgtaaaaga gctgagtcat    2940
gggcttcagt tcgtgatgaa gtggacaaaa tggtccggtc ggtctcttgt aacgttggta    3000
agctacttca catattcacc actcttgcta tatatatgtg caattaaaca aatatgtaaa    3060
aagtgaaagt actcatttct tctttcttta gtatgtactt taacatttaa ccaaaacaat    3120
tgtaggtaag cctataaacg tcggggagca aattttttgca ctgacccgca acataactta    3180
ccgggcagcg tttgggtcag cctgcgaaga gggacaagac gagttcataa gaatcttaca    3240
agagttctct aagcttttg gagccttcaa cgtagcggat ttcataccat atttcgggtg    3300
gatcgatccg caagggataa acaagcggct cgtgaaggcc cgtaatgatc tagacggatt    3360
tattgacgat attatcgatg aacatatgaa gaagaaggag aatcaaaacg ctgtggatga    3420
tggggatgtt gtcgataccg atatggttga tgatcttctt gcttttttaca gtgaagaggc    3480 caaattagtc agtgagacag cggatcttca aaattccatc aaacttaccc gtgacaatat    3540
caaagcaatc atcatggtaa ttatatttca aaaagcacta gtcatagtca tgtttcttaa    3600
tgcgttacgt aataatactt atccattgac cagttatttt ctcctaagtt tttttgtttg    3660
aattaggaag gtaattttct attttactag agaaagcaac agattttagc atgatctttt    3720
tttaatatat atagaagcat tgaatattca gatctacaat aattatgaaa ctaatgaaga    3780
gacaaaaaat ggagagagaa aaagaaaga gtggactagt gtggatatat ttaattctaa    3840
tttgatttta ttaggacgtt atatttaatt ctaatttgat ttttttattt gattttatta    3900
ggacgttatg tttggaggaa cggaaacggt agcgtcggcg atagagtggg ccttaacgga    3960
gttattacgg agccccgagg atctaaaacg ggtccaacaa gaactcgccg aagtcgttgg    4020
acttgacaga cgagttgaag aatccgacat cgagaagttg acttatctca aatgcacact    4080
caaagaaacc ctaaggatgc acccaccgat ccctctcctc ctccacgaaa ccgcggagga    4140
cactagtatc gacggtttct tcattcccaa gaaatctcgt gtgatgatca acgcgtttgc    4200
cataggacgc gacccaacct cttggactga cccggcacg tttagaccat cgaggttttt    4260
ggaaccgggc gtaccggatt tcaaagggag caatttcgag tttataccgt tcgggtcggg    4320
tcgtagatcg tgcccgggta tgcaactagg gttatacgcg cttgacttag ccgtggctca    4380
tatattacat tgcttcacgt ggaaattacc tgatgggatg aaaccaagtg agctcgacat    4440
gaatgatgtg tttggtctca cggctcctaa agccacgcgg cttttcgccg tgccaaccac    4500
gcgcctcatc tgtgctcttt aagtttatgg ttcgagtcac gtggcagggg gtttggtatg    4560
gtgaaaactg aaaagtttga agttgccctc atcgaggatt tgtggatgtc atatgtatgt    4620
```

-continued

```
atgtgtatac acgtgtgttc tgatgaaaac agatttggct ctttgtttgc ccttttttt      4680 tttttcttta atgggatttt tccttgaatg aaatgtaaca gtaaaaataa gattttttc      4740 aataagtaat ttagcatgtt gcaaagatcg atcttggatg agaacttcta cttaaaaaaa      4800
aaaaaaaaat ttttttttag ttatttcacc tttttcttt gttctggttg tatggttgcc      4860
attgtgtcaa ttagggctg gaagttcgct ggttaaggct aaatcagagt taagttata      4920 attttacaag cccaacaaaa ggtcgcagat taaaaccaca tgatatttat aaaaaaatt      4980 ctaaggtttt tattagtttt attttcagtt tactgagtac tatttacttt tttatttttt      5040
gcaaataaat gtattttatc atatttatgt ttttgttat aaactccaaa catacaggtt      5100
tcattaccta aaaaaagaca gagtggtttc gttaattttg tttcattaat ctcgag         5156
```

<210> SEQ ID NO 4
<211> LENGTH: 520
<212> TYPE: PRT
<213> ORGANISM: Arabidopsis thaliana

<400> SEQUENCE: 4

```
Met Glu Ser Ser Ile Ser Gln Thr Leu Ser Lys Leu Ser Asp Pro Thr
  1               5                  10                  15

Thr Ser Leu Val Ile Val Val Ser Leu Phe Ile Phe Ile Ser Phe Ile
             20                  25                  30

Thr Arg Arg Arg Arg Pro Pro Tyr Pro Pro Gly Pro Arg Gly Trp Pro
         35                  40                  45

Ile Ile Gly Asn Met Leu Met Met Asp Gln Leu Thr His Arg Gly Leu
     50                  55                  60

Ala Asn Leu Ala Lys Lys Tyr Gly Gly Leu Cys His Leu Arg Met Gly
 65                  70                  75                  80

Phe Leu His Met Tyr Ala Val Ser Ser Pro Glu Val Ala Arg Gln Val
                 85                  90                  95

Leu Gln Val Gln Asp Ser Val Phe Ser Asn Arg Pro Ala Thr Ile Ala
            100                 105                 110

Ile Ser Tyr Leu Thr Tyr Asp Arg Ala Asp Met Ala Phe Ala His Tyr
        115                 120                 125

Gly Pro Phe Trp Arg Gln Met Arg Lys Val Cys Val Met Lys Val Phe
    130                 135                 140

Ser Arg Lys Arg Ala Glu Ser Trp Ala Ser Val Arg Asp Glu Val Asp
145                 150                 155                 160

Lys Met Val Arg Ser Val Ser Cys Asn Val Gly Lys Pro Ile Asn Val
                165                 170                 175

Gly Glu Gln Ile Phe Ala Leu Thr Arg Asn Ile Thr Tyr Arg Ala Ala
            180                 185                 190

Phe Gly Ser Ala Cys Glu Lys Gly Gln Asp Glu Phe Ile Arg Ile Leu
        195                 200                 205

Gln Glu Phe Ser Lys Leu Phe Gly Ala Phe Asn Val Ala Asp Phe Ile
    210                 215                 220

Pro Tyr Phe Gly Trp Ile Asp Pro Gln Gly Ile Asn Lys Arg Leu Val
225                 230                 235                 240

Lys Ala Arg Asn Asp Leu Asp Gly Phe Ile Asp Ile Ile Asp Glu
                245                 250                 255

His Met Lys Lys Lys Glu Asn Gln Asn Ala Val Asp Asp Gly Asp Val
            260                 265                 270

Val Asp Thr Asp Met Val Asp Asp Leu Leu Ala Phe Tyr Ser Glu Glu
```

-continued

```
                       275                 280                 285
Ala Lys Leu Val Ser Glu Thr Ala Asp Leu Gln Asn Ser Ile Lys Leu
        290                 295                 300

Thr Arg Asp Asn Ile Lys Ala Ile Ile Met Asp Val Met Phe Gly Gly
305                 310                 315                 320

Thr Glu Thr Val Ala Ser Ala Ile Glu Trp Ala Leu Thr Glu Leu Leu
                325                 330                 335

Arg Ser Pro Glu Asp Leu Lys Arg Val Gln Gln Glu Leu Ala Glu Val
                340                 345                 350

Val Gly Leu Asp Arg Arg Val Glu Glu Ser Asp Ile Glu Lys Leu Thr
        355                 360                 365

Tyr Leu Lys Cys Thr Leu Lys Glu Thr Leu Arg Met His Pro Pro Ile
        370                 375                 380

Pro Leu Leu Leu His Glu Thr Ala Glu Asp Thr Ser Ile Asp Gly Phe
385                 390                 395                 400

Phe Ile Pro Lys Lys Ser Arg Val Met Ile Asn Ala Phe Ala Ile Gly
                405                 410                 415

Arg Asp Pro Thr Ser Trp Thr Asp Pro Asp Thr Phe Arg Pro Ser Arg
                420                 425                 430

Phe Leu Glu Pro Gly Val Pro Asp Phe Lys Gly Ser Asn Phe Glu Phe
        435                 440                 445

Ile Pro Phe Gly Ser Gly Arg Arg Ser Cys Pro Gly Met Gln Leu Gly
        450                 455                 460

Leu Tyr Ala Leu Asp Leu Ala Val Ala His Ile Leu His Cys Phe Thr
465                 470                 475                 480

Trp Lys Leu Pro Asp Gly Met Lys Pro Ser Glu Leu Asp Met Asn Asp
                485                 490                 495

Val Phe Gly Leu Thr Ala Pro Lys Ala Thr Arg Leu Phe Ala Val Pro
                500                 505                 510

Thr Thr Arg Leu Ile Cys Ala Leu
        515                 520

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
ccattatagt ttgtgtatcc gc                                            22
```